US009415209B2

(12) United States Patent  
Fisk et al.

(10) Patent No.: US 9,415,209 B2
(45) Date of Patent: Aug. 16, 2016

(54) METHODS OF MANUFACTURING DEVICES FOR THE NEUROREHABILITATION OF A PATIENT

(71) Applicant: Neurohabilitation Corporation, Newtown, PA (US)

(72) Inventors: Justin Fisk, Providence, RI (US); Mark Guarraia, Cranston, RI (US); Aidan Petrie, Jamestown, RI (US); Joseph M. Gordon, Mansfield, MA (US); Faith David-Hegerich, Holliston, MA (US); Shane Siwinski, Providence, RI (US); Adam Muratori, Greenville, RI (US); Jeffrey M. Wallace, Saunderstown, RI (US)

(73) Assignee: Neurohabilitation Corporation, Newtown, PA (US)

( * ) Notice: Subject to any disclaimer, the term of this patent is extended or adjusted under 35 U.S.C. 154(b) by 0 days.

(21) Appl. No.: 14/559,080

(22) Filed: Dec. 3, 2014

(65) Prior Publication Data

US 2016/0158535 A1 Jun. 9, 2016

(51) Int. Cl.
*A61N 1/00* (2006.01)
*A61N 1/05* (2006.01)
*A61N 1/36* (2006.01)

(52) U.S. Cl.
CPC .......... *A61N 1/0548* (2013.01); *A61N 1/36067* (2013.01); *A61N 1/36082* (2013.01); *A61N 1/36103* (2013.01)

(58) Field of Classification Search
USPC ......................................................... 607/134
See application file for complete search history.

(56) References Cited

U.S. PATENT DOCUMENTS

| 2,055,540 | A | 9/1936 | Karnofsky |
| 3,851,651 | A | 12/1974 | Icenbice, Jr. |
| 4,865,048 | A | 9/1989 | Eckerson |
| 4,924,880 | A | 5/1990 | O'Neill et al. |
| 4,995,404 | A | 2/1991 | Nemir |
| 5,259,762 | A | 11/1993 | Farrell |
| 5,265,624 | A | 11/1993 | Bowman |

(Continued)

FOREIGN PATENT DOCUMENTS

WO 02066111 A1 8/2002

OTHER PUBLICATIONS

Danilov, Y.P., et al., Emerging Noninvasive Neurostimulation Technologies: CN-NINM and Sympatocorection, Journal of Behavioral and Brain Science, 2014, 4, pp. 105-113.

(Continued)

*Primary Examiner* — Nicole F Lavert
(74) *Attorney, Agent, or Firm* — Proskauer Rose LLP

(57) ABSTRACT

A mouthpiece for providing non-invasive neuromodulation to a patient, the mouthpiece including an elongated housing having an anterior region and a posterior region, the elongated housing having a non-planar exterior top surface and internal structural members disposed within the housing, the internal structural members elastically responding to biting forces generated by the patient, a spacer attached to the top surface of the housing for limiting contact between a patient's upper teeth and the exterior top surface of the elongated housing, and a printed circuit board mounted to a bottom portion of the elongated housing, the printed circuit board having a plurality of electrodes for delivering subcutaneous local electrical stimulation to the patient's tongue.

20 Claims, 28 Drawing Sheets

(56) References Cited

U.S. PATENT DOCUMENTS

| | | |
|---|---|---|
| 5,269,303 A | 12/1993 | Wernicke et al. |
| 5,299,569 A | 4/1994 | Wernicke et al. |
| 5,540,734 A | 7/1996 | Zabara |
| 5,553,626 A | 9/1996 | Burger et al. |
| 5,792,067 A | 8/1998 | Karell |
| 5,794,621 A | 8/1998 | Hogan et al. |
| 5,878,154 A | 3/1999 | Schimmelpfennig |
| D409,307 S | 5/1999 | Phleps et al. |
| 6,066,163 A | 5/2000 | John |
| 6,089,864 A | 7/2000 | Buckner et al. |
| 6,161,044 A | 12/2000 | Silverstone |
| D437,058 S | 1/2001 | Gozani |
| 6,169,781 B1 | 1/2001 | Doebert |
| 6,267,733 B1 | 7/2001 | Peterson et al. |
| D449,376 S | 10/2001 | McDonald et al. |
| D449,883 S | 10/2001 | McDonald et al. |
| D451,598 S | 12/2001 | McDonald et al. |
| 6,326,901 B1 | 12/2001 | Gonzales |
| 6,339,725 B1 | 1/2002 | Naritoku et al. |
| 6,366,813 B1 | 4/2002 | DiLorenzo |
| 6,366,814 B1 | 4/2002 | Boveja et al. |
| 6,405,079 B1 | 6/2002 | Ansarinia |
| 6,430,450 B1 | 8/2002 | Bach-y-Rita et al. |
| D462,357 S | 9/2002 | Jenkins |
| 6,463,328 B1 | 10/2002 | John |
| 6,526,318 B1 | 2/2003 | Ansarinia |
| 6,546,291 B2 | 4/2003 | Merfeld et al. |
| 6,556,868 B2 | 4/2003 | Naritoku et al. |
| 6,954,668 B1 | 10/2005 | Cuozzo |
| D515,697 S | 2/2006 | Nakamura et al. |
| D531,314 S | 10/2006 | Atkinson et al. |
| D542,408 S | 5/2007 | Oldenburg et al. |
| 7,228,178 B2 | 6/2007 | Carroll et al. |
| 7,236,830 B2 | 6/2007 | Gliner |
| D555,252 S | 11/2007 | Kitayama et al. |
| D557,685 S | 12/2007 | Lee et al. |
| 7,333,020 B2 | 2/2008 | Cohen et al. |
| D565,184 S | 3/2008 | Royzen |
| D575,268 S | 8/2008 | Christopher et al. |
| D578,222 S | 10/2008 | Sakurai et al. |
| D579,552 S | 10/2008 | Oldenburg et al. |
| 7,483,747 B2 | 1/2009 | Gliner et al. |
| D593,067 S | 5/2009 | Millora et al. |
| 7,563,929 B2 | 7/2009 | Hobbs et al. |
| 7,640,062 B2 | 12/2009 | Shalev |
| 7,672,730 B2 | 3/2010 | Firlik et al. |
| 7,725,192 B2 | 5/2010 | Eskandar et al. |
| D617,308 S | 6/2010 | Nousiainen et al. |
| 7,747,325 B2 | 6/2010 | Dilorenzo |
| D624,189 S | 9/2010 | Rutt et al. |
| D663,714 S | 7/2012 | Kang et al. |
| D669,881 S | 10/2012 | Clements et al. |
| 8,290,582 B2 | 10/2012 | Lin et al. |
| D687,018 S | 7/2013 | Afshar |
| D706,745 S | 6/2014 | Nakagawa |
| D707,199 S | 6/2014 | Cepress et al. |
| D709,673 S | 7/2014 | Aimone et al. |
| D710,718 S | 8/2014 | Ichihashi et al. |
| 8,805,548 B2 | 8/2014 | Mignolet et al. |
| D713,531 S | 9/2014 | Way et al. |
| 8,849,407 B1 | 9/2014 | Danilov et al. |
| D716,759 S | 11/2014 | Ha et al. |
| D721,673 S | 1/2015 | Park et al. |
| D723,510 S | 3/2015 | Ishikura |
| D724,197 S | 3/2015 | Hughes |
| D725,262 S | 3/2015 | Chowdhury |
| D728,109 S | 4/2015 | Ko |
| D730,867 S | 6/2015 | Park et al. |
| D731,999 S | 6/2015 | Cepress et al. |
| D739,122 S | 9/2015 | Aimone et al. |
| D744,658 S | 12/2015 | Hilkey-Boyatt |
| 2004/0073270 A1 | 4/2004 | Firlik et al. |
| 2005/0089829 A1 | 4/2005 | Wasowicz |
| 2005/0240253 A1 | 10/2005 | Tyler et al. |
| 2006/0161218 A1 | 7/2006 | Danilov |
| 2006/0241718 A1 | 10/2006 | Tyler et al. |
| 2007/0248238 A1 | 10/2007 | Abreu |
| 2007/0250119 A1 | 10/2007 | Tyler et al. |
| 2007/0293917 A1 | 12/2007 | Thompson et al. |
| 2008/0009772 A1 | 1/2008 | Tyler et al. |
| 2008/0027510 A1 | 1/2008 | McClure et al. |
| 2008/0082131 A1 | 4/2008 | Llanos |
| 2008/0208287 A1 | 8/2008 | Palermo et al. |
| 2008/0222670 A1 | 9/2008 | Lee et al. |
| 2008/0228239 A1 | 9/2008 | Tyler et al. |
| 2008/0233541 A1* | 9/2008 | De Vreese ........... A61C 19/066 433/216 |
| 2008/0281550 A1 | 11/2008 | Hogle et al. |
| 2009/0048647 A1 | 2/2009 | Tingey |
| 2009/0082831 A1 | 3/2009 | Paul et al. |
| 2009/0082839 A1 | 3/2009 | Lindquist et al. |
| 2009/0312808 A1 | 12/2009 | Tyler et al. |
| 2009/0312817 A1 | 12/2009 | Hogle et al. |
| 2009/0326604 A1 | 12/2009 | Tyler et al. |
| 2011/0093036 A1 | 4/2011 | Mashiach |
| 2011/0125184 A1 | 5/2011 | Allen |
| 2011/0201944 A1 | 8/2011 | Higgins et al. |
| 2012/0010672 A1 | 1/2012 | Crespi |
| 2012/0123225 A1 | 5/2012 | Al-Tawil |
| 2012/0165862 A1 | 6/2012 | Allen |
| 2013/0096641 A1 | 4/2013 | Strother et al. |
| 2013/0256345 A1 | 10/2013 | Larkin |
| 2013/0273490 A1 | 10/2013 | Way et al. |
| 2014/0039579 A1 | 2/2014 | Mashiach et al. |
| 2014/0135868 A1 | 5/2014 | Bashyam |
| 2014/0172041 A1 | 6/2014 | Draghici et al. |
| 2014/0194946 A1 | 7/2014 | Thomas et al. |
| 2014/0379049 A1 | 12/2014 | Mashiach et al. |
| 2015/0057719 A1 | 2/2015 | Tang |
| 2015/0264474 A1 | 9/2015 | Seo et al. |

OTHER PUBLICATIONS

Tyler, M.E., et al., "Non-invasive Neuromodulation to improve gait in chronic multiple sclerosis: a randomized double blind controlled pilot trial," Journal of Neuroengineering and Rehabilitation, 2014, pp. 1-10.

Interchange PoNS Unit. Helius Medical technologies, Inc. Listing Statement; Jun. 20, 2014; 3 pages; [retrieved on Nov. 16, 2015] Retrieved from the Internet: http://www.cnsx.ca/cmsAssets/docs/Filings/2014/2014_06_20_20_39_31_HSM_Helius_Form_2A Listing_Statement.pdf.

The PoNS Device, Helius Medical Technologies, Inc.; 2015; 4 pages; [retrieved on Dec. 2, 2015]; Retrieved from the Internet URL: http://www.heliusmedical.com/divisions/neurohabilitation/pons-device.

US Army; "Mouth Device in Clinical Trials as Possible Treatment for TBI;" Feb. 14, 2013; 2 pages; [retrieved on Dec. 2, 2015]. Retrieved from the Internet URL: http://www.army.mil/article/96521/Mouth_device-in_clinical_trials_as_possible_treatment_for_TBI.

* cited by examiner

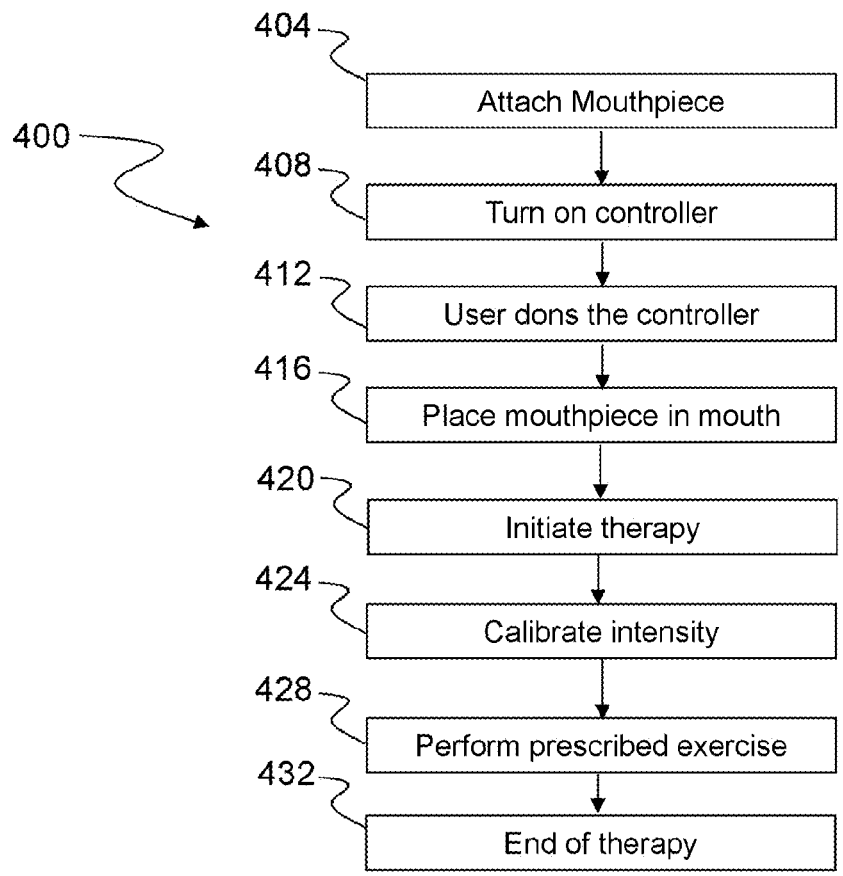

METHODS OF MANUFACTURING DEVICES FOR THE NEUROREHABILITATION OF A PATIENT

FIELD OF THE INVENTION

In general, the invention relates to devices and methods for non-invasive neurostimulation of a subject's brain. More specifically, the invention relates to devices and methods for non-invasive neurostimulation of a subject's brain to effect treatment of various maladies.

BACKGROUND OF THE INVENTION

Traumatic brain injury (TBI) is a leading cause of disability around the world. Each year in the United States, about two million people suffer a TBI, with many suffering long term symptoms. Long term symptoms can include impaired attention, impaired judgment, reduced processing speed, and defects in abstract reasoning, planning, problem-solving and multitasking.

A stroke is a loss of brain function due to a disturbance in the blood supply to the brain. Every year, about 800,000 people in the United States will have a stroke. Stroke is a leading cause of long-term disability in the United States, with nearly half of older stroke survivors experiencing moderate to severe disability. Long term effects can include seizures, incontinence, vision disturbance or loss of vision, dysphagia, pain, fatigue, loss of cognitive function, aphasia, loss of short-term and/or long-term memory, and depression.

Multiple sclerosis (MS) is a disease that causes damage to the nerve cells in the brain and spinal cord. Globally, there are about 2.5 million people who suffer from MS. Symptoms can vary greatly depending on the specific location of the damaged portion of the brain or spinal cord. Symptoms include hypoesthesia, difficulties with coordination and balance, dysarthria, dysphagia, nystagmus, bladder and bowel difficulties, cognitive impairment and major depression to name a few.

Alzheimer's disease (AD) is a neurodegenerative disorder affecting over 25 million people worldwide. Symptoms of AD include confusion, irritability, aggression, mood swings, trouble with language, and both short and long term memory loss. In developed countries, AD is one of the most costly diseases to society.

Parkinson's disease (PD) is a degenerative disorder of the central nervous system, affecting more than 7 million people globally. Symptoms of PD include tremor, bradykinesia, rigidity, postural instability, cognitive disturbances, and behavior and mood alterations.

One approach to treating the long term symptoms associated with TBI, stroke, MS, AD, and PD is neurorehabilitation. Neurorehabilitation involves processes designed to help patients recover from nervous system injuries. Traditionally, neurorehabilitation involves physical therapy (e.g., balance retraining), occupational therapy (e.g., safety training, cognitive retraining for memory), psychological therapy, speech and language therapy, and therapies focused on daily function and community re-integration.

Another approach to treating the long term symptoms associated with TBI, stroke, MS, AD, and PD is neurostimulation. Neurostimulation is a therapeutic activation of part of the nervous system. For example, activation of the nervous system can be achieved through electrical stimulation, magnetic stimulation, or mechanical stimulation. Typical approaches focused mainly on invasive techniques, such as deep brain stimulation (DBS), spinal cord stimulation (SCS), cochlear implants, visual prosthesis, and cardiac electrostimulation devices. Only recently have non-invasive approaches to neurostimulation become more mainstream.

Despite many advances in the areas of neurorehabilitation and neurostimulation, there exists an urgent need for treatments that employ a combined approach, including both neurorehabilitation and neurostimulation to improve the recovery of patients having TBI, stroke, multiple sclerosis, Alzheimer's, Parkinson's, depression, memory loss, compulsive behavior, or any other neurological impairment.

SUMMARY OF THE INVENTION

The invention, in various embodiments, features methods and devices for combining non-invasive neuromodulation with traditional neurorehabilitation therapies. Clinical studies have shown that methods combining neurostimulation with neurorehabilitation are effective in treating the long term neurological impairments due to a range of maladies such as TBI, stroke, MS, AD, and PD.

In one aspect, the invention features a mouthpiece for providing non-invasive neuromodulation to a patient. The mouthpiece includes an elongated housing having an anterior region and a posterior region, the elongated housing having (i) a non-planar exterior top surface and (ii) internal structural members disposed within the housing, the internal structural members elastically responding to biting forces generated by the patient. The mouthpiece also includes a spacer attached to the top surface of the housing for limiting contact between a patient's upper teeth and the exterior top surface of the elongated housing. The mouthpiece also includes a printed circuit board mounted to a bottom portion of the elongated housing, the printed circuit board having a plurality of electrodes for delivering subcutaneous local electrical stimulation to the patient's tongue. In some embodiments, the mouthpiece also includes ribs aligned parallel to a longitudinal axis of the elongated housing. In some embodiments, the mouthpiece also includes ribs aligned perpendicular to a longitudinal axis of the elongated housing. In some embodiments, the mouthpiece also includes ribs aligned parallel to a longitudinal axis of the elongated housing and ribs aligned perpendicular to a longitudinal axis of the elongated housing. In some embodiments, the mouthpiece also includes an interpenetrating network of ribs, with at least some of the ribs aligned parallel to a longitudinal axis of the elongate housing and at least some of the ribs aligned perpendicular to a longitudinal axis of the elongated housing. In some embodiments, the mouthpiece also includes pockets in a posterior portion of the elongated housing formed by the interpenetrating network of ribs. In some embodiments, the mouthpiece also includes integrated circuits located in the pockets. In some embodiments, the ribs have a rectangular cross section. In some embodiments, the ribs are comprised of arches. In some embodiments, the mouthpiece also includes one or more columns extending away from an interior surface of the elongated housing, the one or more columns configured to contact the mounted printed circuit board. In some embodiments, the structural elements can withstand a force of 700 Newtons without causing plastic deformation of the mouthpiece. In some embodiments, the mouthpiece also includes a rectangular sheet embedded on an interior surface of the elongated housing and located in a posterior region of the elongated housing, the rectangular sheet connecting the interpenetrating network of ribs. In some embodiments, the mouthpiece also includes a curvilinear sheet embedded on an interior surface of the elongated housing and located in a region connecting the anterior region and the posterior region of the elongated housing, the curvilinear sheet connecting the ribs aligned parallel to a longitudinal axis of the elongated housing.

In another aspect, the invention features a mouthpiece for providing non-invasive neuromodulation to a patient. The mouthpiece includes an elongated housing having an anterior region and a posterior region, the elongated housing having (i) a non-planar exterior top surface and (ii) internal structural members disposed within the housing, the internal structural members elastically responding to biting forces generated by the patient. The mouthpiece also includes a printed circuit board mounted to a bottom portion of the elongated housing, the printed circuit board having a plurality of electrodes for delivering subcutaneous local electrical stimulation to the patient's tongue. In some embodiments, the mouthpiece also includes ribs aligned parallel to a longitudinal axis of the elongated housing. In some embodiments, the mouthpiece also includes ribs aligned perpendicular to a longitudinal axis of the elongated housing. In some embodiments, the mouthpiece also includes ribs aligned parallel to a longitudinal axis of the elongated housing and ribs aligned perpendicular to a longitudinal axis of the elongated housing. In some embodiments, the mouthpiece also includes an interpenetrating network of ribs, with at least some of the ribs aligned parallel to a longitudinal axis of the elongate housing and at least some of the ribs aligned perpendicular to a longitudinal axis of the elongated housing. In some embodiments, the mouthpiece also includes pockets in a posterior portion of the elongated housing formed by the interpenetrating network of ribs. In some embodiments, the mouthpiece also includes integrated circuits located in the pockets. In some embodiments, the ribs have a rectangular cross section. In some embodiments, the ribs are comprised of arches. In some embodiments, the mouthpiece also includes one or more columns extending away from an interior surface of the elongated housing, the one or more columns configured to contact the mounted printed circuit board. In some embodiments, the structural elements can withstand a force of 700 Newtons without causing plastic deformation of the mouthpiece.

In another aspect, the invention features a mouthpiece for providing non-invasive neuromodulation to a patient. The mouthpiece includes an elongated housing having an anterior region and a posterior region, the elongated housing having a non-planar interior top surface and internal fins located between the non-planar interior top surface and a bottom surface defined by a perimeter of the elongated housing, the internal fins forming a channel at the anterior region of the elongated housing. The mouthpiece also includes a spacer attached to the top surface of the housing for minimizing contact between a patient's upper teeth and the exterior top surface of the elongated housing. The mouthpiece also includes a printed circuit board mounted to a bottom portion of the elongated housing, the printed circuit board having a plurality of electrodes for delivering subcutaneous local electrical stimulation to the patient's tongue. The mouthpiece also includes a cable having a first segment disposed within the housing and a second segment extending from the housing, the cable mounted in an s-shaped pattern along the channel formed by the internal fins, one end of the first segment of the cable connected to the printed circuit board. In some embodiments, the mouthpiece also includes a right angled grommet mounted to an anterior region of the elongated housing, the grommet surrounding the cable as it exits the channel formed by the internal fins, the grommet forcing the cable to make an approximately ninety degree turn as it exits the elongated housing. In some embodiments, the cable forms two consecutive s-shapes along the channel formed by the internal fins. In some embodiments, the mouthpiece also includes a grommet mounted to an anterior region of the elongated housing, the grommet surrounding the cable as it exits the channel formed by the internal fins. In some embodiments, the mouthpiece also includes a cylindrically symmetric elastomeric element, the elastomeric element surrounding a portion of the cable and having trench in a central portion thereof and surrounded by two regions having radii that decrease in relation to a distance from the trench. In some embodiments, the mouthpiece also includes an aperture located at an anterior region of the elongated housing, the aperture configured to form mechanical connection with the trench. In some embodiments, the mouthpiece also includes a cap, the cap having an elastomeric portion in contact with the printed circuit board and a rigid portion in contact with the elongated housing, the cap in cooperation with the elongated housing forming an aperture at an anterior region of the mouthpiece, the aperture configured to form mechanical connection with the trench. In some embodiments, the mouthpiece also includes a valley located in the interior surface of the elongated housing, the valley configured to receive the cable. In some embodiments, the mouthpiece also includes an elastomeric sleeve, the elastomeric sleeve in contact with the cable, and an anterior region of the elongated housing, the elastomeric sleeve providing resistance to bending and tensile strains in the cable.

In another aspect, the invention features a mouthpiece for providing non-invasive neuromodulation to a patient. The mouthpiece includes an elongated housing having an anterior region and a posterior region, the elongated housing having a non-planar interior top surface and a bottom surface defined by a perimeter of the elongated housing. The mouthpiece also includes a spacer attached to the top surface of the elongated housing for minimizing contact between a patient's upper teeth and the exterior top surface of the elongated housing. The mouthpiece also includes a printed circuit board mounted to a bottom portion of the elongated housing, the printed circuit board having a plurality of electrodes for delivering subcutaneous local electrical stimulation to the patient's tongue. The mouthpiece also includes a first elastomeric ring located along an interior sidewall of the elongated housing, the first elastomeric ring forming a sealing surface with the printed circuit board. The mouthpiece also includes a plurality of mechanical protrusions extending from the interior sidewall of the elongated housing, the mechanical protrusions in contact with the printed circuit board. The mouthpiece also includes a cable having a first segment disposed within the housing and a second segment extending from the housing, one end of the first segment of the cable connected to the printed circuit board. In some embodiments, the mouthpiece also includes a valley located in the interior surface of the elongated housing, the valley configured to receive the cable. In some embodiments, the mouthpiece also includes internal fins extending from the interior top surface of the elongated housing, the internal fins forming a channel at an anterior region of the elongated housing. In some embodiments, the cable forms at least two consecutive s-shapes along the channel formed by the internal fins. In some embodiments, the mouthpiece also includes a second elastomeric ring attached to the first elastomeric ring, the second elastomeric ring surrounding a portion of the cable and forming a connection between an anterior portion of the elongated housing and the cable. In some embodiments, the mouthpiece also includes a second elastomeric ring attached to the first elastomeric ring, the second elastomeric ring surrounding a portion of the cable and forming a connection between an anterior portion of the elongated housing and the cable, the second elastomeric ring causing the cable to exit the mouthpiece at an angle of 90 degrees.

In another aspect, the invention features a mouthpiece for providing non-invasive neuromodulation to a patient. The mouthpiece includes an elongated housing having an anterior region and a posterior region, the elongated housing having a non-planar interior top surface and internal fins located between the non-planar interior top surface and a bottom surface defined by a perimeter of the elongated housing, the internal fins forming a channel at the anterior region of the elongated housing. The mouthpiece also includes a printed circuit board mounted to a bottom portion of the elongated housing, the printed circuit board having a plurality of electrodes for delivering subcutaneous local electrical stimulation to the patient's tongue. The mouthpiece also includes a cable having a first segment disposed within the housing and a second segment extending from the housing, the cable mounted in an s-shaped pattern along the channel formed by the internal fins, one end of the first segment of the cable connected to the printed circuit board. In some embodiments, the mouthpiece also includes a right angled grommet mounted to an anterior region of the elongated housing, the grommet surrounding the cable as it exits the channel formed by the internal fins, the grommet forcing the cable to make an approximately ninety degree turn as it exits the elongated housing. In some embodiments, the cable forms two consecutive s-shapes along the channel formed by the internal fins. In some embodiments, the mouthpiece also includes a grommet mounted to an anterior region of the elongated housing, the grommet surrounding the cable as it exits the channel formed by the internal fins. In some embodiments, the mouthpiece also includes a cylindrically symmetric elastomeric element, the elastomeric element surrounding a portion of the cable and having trench in a central portion thereof and surrounded by two regions having radii that decrease in relation to a distance from the trench. In some embodiments, the mouthpiece also includes an aperture located at an anterior region of the elongated housing, the aperture configured to form mechanical connection with the trench. In some embodiments, the mouthpiece also includes a cap, the cap having an elastomeric portion in contact with the printed circuit board and a rigid portion in contact with the elongated housing, the cap in cooperation with the elongated housing forming an aperture at an anterior region of the mouthpiece, the aperture configured to form mechanical connection with the trench. In some embodiments, the mouthpiece also includes a valley located in the interior surface of the elongated housing, the valley configured to receive the cable. In some embodiments, the mouthpiece also includes an elastomeric sleeve, the elastomeric sleeve in contact with the cable, and an anterior region of the elongated housing, the elastomeric sleeve providing resistance to bending and tensile strains in the cable.

In another aspect, the invention features a mouthpiece for providing non-invasive neuromodulation to a patient. The mouthpiece includes an elongated housing having an anterior region and a posterior region, the elongated housing having a non-planar exterior top surface. The mouthpiece also includes a spacer attached to the top surface of the housing for minimizing contact between a patient's upper teeth and the exterior top surface of the elongated housing. The mouthpiece also includes a first printed circuit board mounted to a bottom portion of the elongated housing, the first printed circuit board having a plurality of electrodes for delivering subcutaneous local electrical stimulation to the patient's tongue. The mouthpiece also includes a rim extending from a bottom portion of the elongated housing, the rim surrounding a perimeter of the first printed circuit board and having a u-shaped cross section. The mouthpiece also includes a well shaped to accommodate an adhesive, the adhesive bonding the first printed circuit board to the elongate housing. In some embodiments, a portion of the rim rests below the first printed circuit board and prevents a patient's teeth from contacting the printed circuit board. In some embodiments, the first printed circuit board is non-planar and the plurality of electrodes are located on a non-planar surface of the first printed circuit board. In some embodiments, the first printed circuit board has a curved shape and the plurality of electrodes are located on a curved surface of the first printed circuit board. In some embodiments, the plurality of electrodes has a first density at an anterior region of the first printed circuit board and a second density at a posterior region of the first printed circuit board, wherein the first density is greater than the second density. In some embodiments, the mouthpiece also includes a second printed circuit board mounted above the first printed circuit board. In some embodiments, the rim is an integral part of the elongated housing. In some embodiments, the rim is dimensioned to define the glue well between the bottom portion of the elongated housing and the perimeter of the first printed circuit board. In some embodiments, the rim is concentric with the perimeter of the first printed circuit board. In some embodiments, the rim covers a bottom portion of the first printed circuit board along the perimeter thereof. In some embodiments, the rim covers a side portion of the first printed circuit board along the perimeter thereof. In some embodiments, the rim covers a bottom portion and a side portion of the first printed circuit board along the perimeter thereof.

In another aspect, the invention features a mouthpiece for providing non-invasive neuromodulation to a patient. The mouthpiece includes an elongated housing having an anterior region and a posterior region, the elongated housing having a non-planar exterior top surface. The mouthpiece also includes a spacer attached to the top surface of the housing for minimizing contact between a patient's upper teeth and the exterior top surface of the elongated housing. The mouthpiece also includes a first printed circuit board mounted to a bottom portion of the elongated housing, the first printed circuit board having a plurality of electrodes for delivering subcutaneous local electrical stimulation to the patient's tongue. The mouthpiece also includes a rim extending from a bottom portion of the elongated housing, the rim surrounding a perimeter of the first printed circuit board. The mouthpiece also includes a beveled well configured to accommodate an adhesive, the adhesive bonding at least two orthogonal surfaces of the first printed circuit board to the elongated housing. In some embodiments, a portion of the rim rests below the first printed circuit board and prevents a patient's teeth from contacting the first printed circuit board. In some embodiments, the first printed circuit board is non-planar and the plurality of electrodes are located on a non-planar surface of the first printed circuit board. In some embodiments, the first printed circuit board has a curved shape and the plurality of electrodes are located on a curved surface of the first printed circuit board. In some embodiments, the plurality of electrodes has a first density at an anterior region of the first printed circuit board and a second density at a posterior region of the first printed circuit board, wherein the first density is greater than the second density. In some embodiments, the mouthpiece also includes a second printed circuit board mounted above the first printed circuit board. In some embodiments, the rim is an integral part of the elongated housing. In some embodiments, the rim is dimensioned to define the glue well between the bottom portion of the elongated housing and the perimeter of the first printed circuit board. In some embodiments, the rim is concentric with the perimeter of the first printed circuit board. In some embodiments, the rim covers a bottom portion of the first printed circuit board along the perimeter thereof. In some embodiments, the rim covers a side portion of the first printed circuit board along the perimeter thereof. In some embodiments, the rim covers a bottom portion and a side portion of the first printed circuit board along the perimeter thereof.

In another aspect, the invention features a method of manufacturing a mouthpiece, the mouthpiece providing non-invasive neuromodulation to a patient. The method includes providing an elongated housing having internal fins located between a non-planar interior top surface and a bottom surface defined by a perimeter of the elongated housing, the internal fins forming a channel at the anterior region of the elongated housing. The method also includes attaching a spacer to the top surface of the elongated housing for minimizing contact between a patient's upper teeth and the exterior top surface of the elongated housing. The method also includes mounting a cable in an s-shaped pattern along the channel formed by the internal fins. The method also includes mounting a printed circuit board to a bottom portion of the elongated housing, the printed circuit board having a plurality of electrodes for delivering subcutaneous local electrical stimulation to the patient's tongue. The method also includes connecting one end of the cable to the printed circuit board. In some embodiments, the method also includes forming a 90 degree bend in the cable at an exit of elongated housing. In some embodiments, the method also includes threading the cable through an elastomeric element located at the exit of the elongated housing. In some embodiments, the method also includes forming two consecutive s-shapes along the cable. In some embodiments, the method also includes mounting a cylindrically symmetric elastomeric element to the cable, the elastomeric element surrounding a portion of the cable and having a trench in a central portion thereof and surrounded by two regions having radii that decrease in relation to a distance from the trench. In some embodiments, the method also includes forming an aperture at an anterior region of the elongated housing, the aperture configured to form mechanical connection with the trench. In some embodiments, the method also includes providing a cap having an elastomeric portion and a rigid portion. In some embodiments, the method also includes contacting the elastomeric portion of the cap with the printed circuit board and contacting the rigid portion of the cap with the elongated housing. In some embodiments, the method also includes cooperatively forming an aperture with the cap and the elongated housing, the aperture forming a mechanical connection with the trench. In some embodiments, the method also includes forming a valley located in the interior surface of the elongated housing. In some embodiments, the method also includes receiving a cable in the valley. In some embodiments, the method also includes forming an elastomeric sleeve around the cable, the elastomeric sleeve in contact with an anterior region of the elongated housing, the elastomeric sleeve providing resistance to bending and tensile strains in the cable. In some embodiments, the method also includes applying an adhesive along the perimeter of the printed circuit board, the adhesive bonding at least two orthogonal surfaces of the first printed circuit board to the elongated housing.

In another aspect, the invention features a method of manufacturing a mouthpiece, the mouthpiece providing non-invasive neuromodulation to a patient. The method includes providing an elongated housing having a plurality of mechanical protrusions extending from an interior sidewall thereof and first elastomeric ring located along an interior sidewall of the elongated housing. The method also includes attaching a spacer to the top surface of the elongated housing for minimizing contact between a patient's upper teeth and a top surface of the elongated housing. The method also includes contacting a printed circuit board to the first elastomeric ring of the elongated housing to form a seal, the printed circuit board having a plurality of electrodes for delivering subcutaneous local electrical stimulation to the patient's tongue. The method also includes providing a cable having a first segment disposed within the housing and a second segment extending from the housing. The method also includes connecting one end of the first segment of the cable connected to the printed circuit board. In some embodiments, the method also includes forming a 90 degree bend in the cable at an exit of elongated housing. In some embodiments, the method also includes threading the cable through an elastomeric element located at the exit of the elongated housing. In some embodiments, the method also includes forming two consecutive s-shapes along the cable. In some embodiments, the method also includes mounting a cylindrically symmetric elastomeric element to the cable, the elastomeric element surrounding a portion of the cable and having a trench in a central portion thereof and surrounded by two regions having radii that decrease in relation to a distance from the trench. In some embodiments, the method also includes forming an aperture at an anterior region of the elongated housing, the aperture configured to form mechanical connection with the trench. In some embodiments, the method also includes forming a valley located in the interior surface of the elongated housing. In some embodiments, the method also includes receiving a cable in the valley. In some embodiments, the method also includes forming an elastomeric sleeve around the cable, the elastomeric sleeve in contact with an anterior region of the elongated housing, the elastomeric sleeve providing resistance to bending and tensile strains in the cable.

As used herein, the terms "approximately," "roughly," and "substantially" mean ±10%, and in some embodiments, ±5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

The advantages of the invention described above, together with further advantages, may be better understood by referring to the following description taken in conjunction with the accompanying drawings. The drawings are not necessarily to scale, emphasis instead generally being placed upon illustrating the principles of the invention.

FIG. 4A is a flow chart illustrating a method in accordance with one embodiment for operating a neurostimulation system.

FIG. 4B is a flow chart illustrating a method in accordance with one embodiment for operating a neurostimulation system.

DETAILED DESCRIPTION

Figure 1:
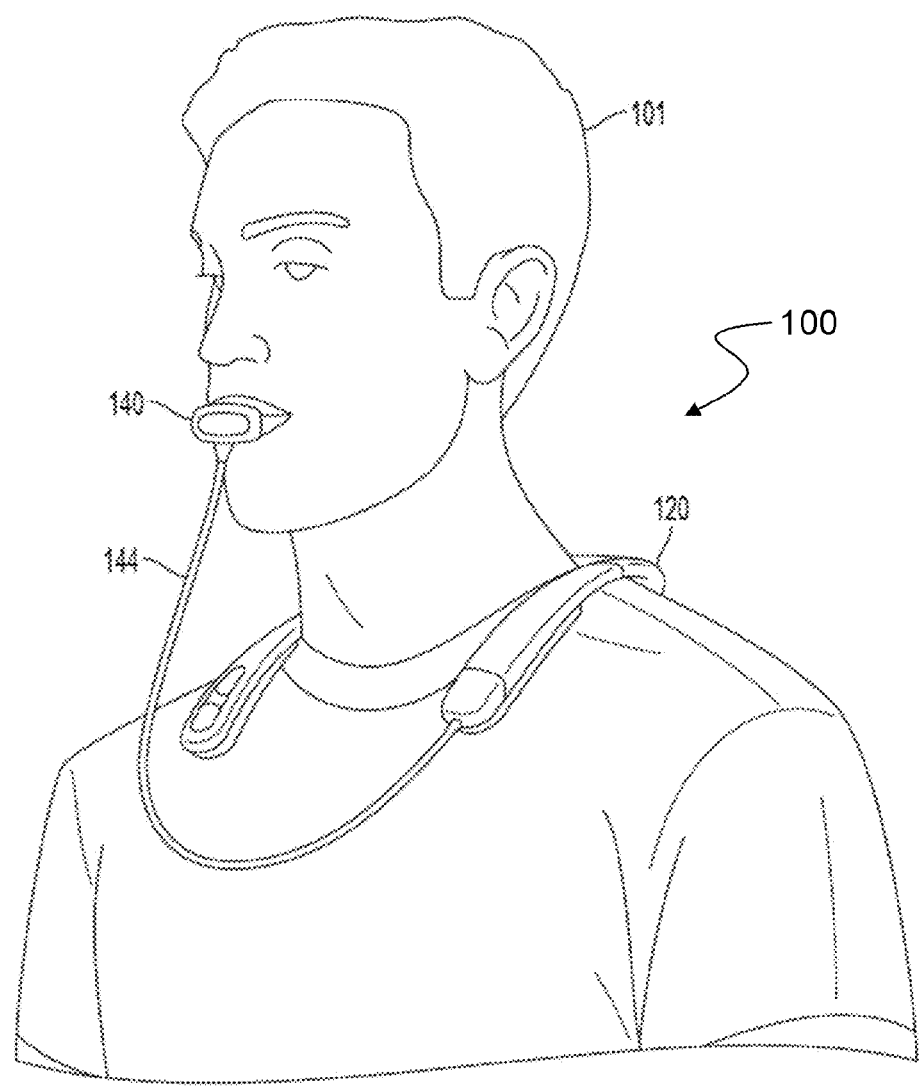
FIG. 1 is a drawing of a patient engaged in a non-invasive neurostimulation therapy session according to an illustrative embodiment of the invention.

FIG. 1 shows a patient 101 undergoing non-invasive neuromodulation therapy (NINM) using a neurostimulation system 100. During a therapy session, the neurostimulation system 100 non-invasively stimulates various nerves located within the patient's oral cavity, including at least one of the trigeminal and facial nerves. In combination with the NINM, the patient engages in an exercise or other activity specifically designed to assist in the neurorehabilitation of the patient. For example, the patient can perform a physical therapy routine (e.g., moving an affected limb, or walking on a treadmill) engage in a mental therapy (e.g., meditation or breathing exercises), or a cognitive exercise (e.g., computer assisted memory exercises) during the application of NINM. The combination of NINM with an appropriately chosen exercise or activity has been shown to be useful in treating a range of maladies including, for example, traumatic brain injury, stroke (TBI), multiple sclerosis (MS), balance, gait, vestibular disorders, visual deficiencies, tremor, headache, migraines, neuropathic pain, hearing loss, speech recognition, auditory problems, speech therapy, cerebral palsy, blood pressure, relaxation, and heart rate. For example, a useful non-invasive neuromodulation (NINM) therapy routine has been recently developed as described in U.S. Pat. No. 8,849, 407, the entirety of which is incorporated herein by reference.

Figure 2A:
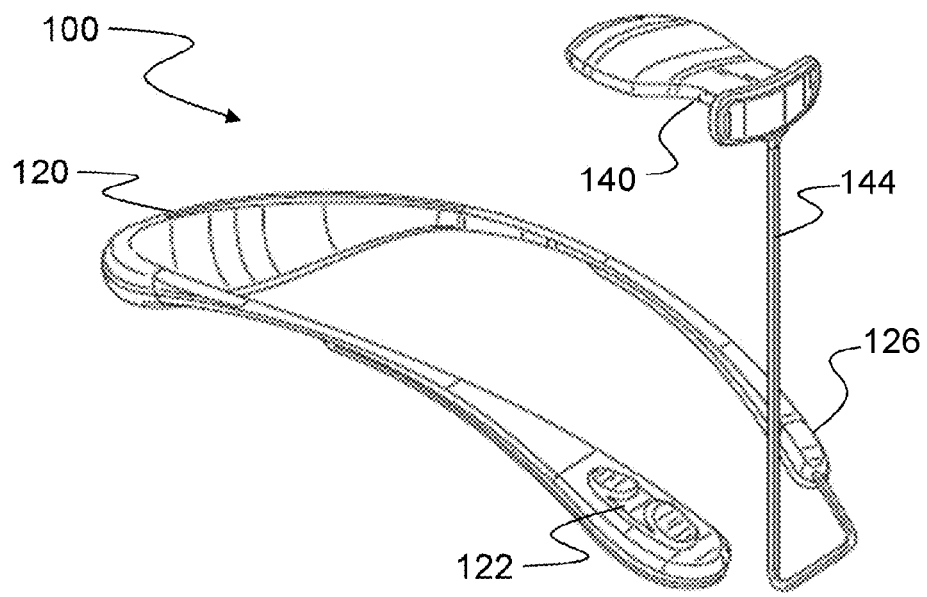
FIGS. 2A and 2B are diagrams showing a neurostimulation system according to an illustrative embodiment of the invention.
Figure 2B:
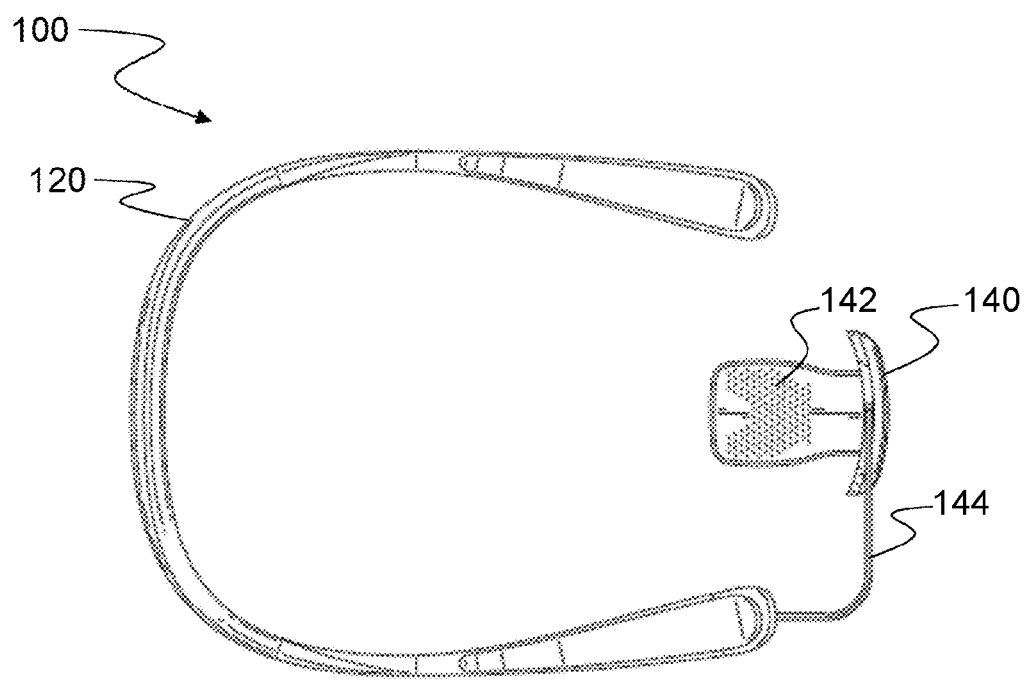

FIGS. 2A and 2B show a non-invasive neurostimulation system 100. The non-invasive neurostimulation system 100 includes a controller 120 and a mouthpiece 140.

The controller 120 includes a receptacle 126 and pushbuttons 122. The mouthpiece 140 includes an electrode array 142 and a cable 144. The cable 144 connects to the receptacle 126, providing an electrical connection between the mouthpiece 140 and the controller 120. In some embodiments, the controller 120 includes a cable. In some embodiments, the mouthpiece 140 and the controller 120 are connected wirelessly (e.g., without the use of a cable). During operation, a patient activates the neurostimulation system 100 by actuating one of the pushbuttons 122. In some embodiments, the neurostimulation system 100 periodically transmits electrical pulses to determine if the electrode array 142 is in contact with the patient's tongue and automatically activates based on the determination. After activation, the patient can start an NINM treatment session, stop the NINM treatment session, or pause the NINM treatment session by pressing one of the pushbuttons 122. In some embodiments, the neurostimulation system 100 periodically transmits electrical pulses to determine if the electrode array 142 is in contact with the patient's tongue and automatically pauses the NINM treatment session based on the determination. During an NINM treatment session, the patient engages in an exercise or other activity designed to facilitate neurorehabilitation. For example, during an NINM treatment session, the patient can engage in a physical exercise, a mental exercise, or a cognitive exercise. In some embodiments, the controller 120 has pushbuttons on both arms. In some embodiments, a mobile device can be used in conjunction with the controller 120 and the mouthpiece 140. The mobile device can include a software application that allows a user to activate the neurostimulation system 100 and start or stop an NINM treatment session by for example, pressing a button on the mobile device, or speaking a command into the mobile device. The mobile device can obtain patient information and treatment session information before, during, or after an NINM treatment session. In some embodiments, the controller 120 includes a secure cryptoprocessor that holds a secret key, to be described in more detail below in connection with FIGS. 9A and 9B. The secure cryptoprocessor is in communication with a microcontroller. The secure cryptoprocessor can be tamper proof. For example, if outer portions of the cryptoprocessor are removed in an attempt to access the secret key, the cryptoprocessor erases all memory, preventing unauthorized access of the secret key.

Figure 2C:
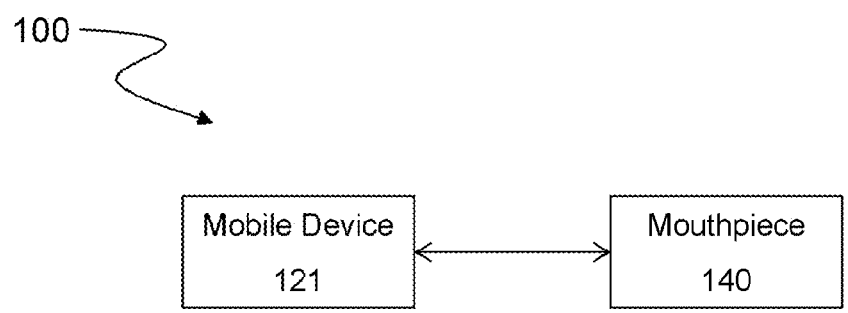
FIG. 2C is a diagram showing a neurostimulation system according to an illustrative embodiment of the invention.

FIG. 2C shows a non-invasive neurostimulation system 100. As shown, a mobile device 121 is in communication with a mouthpiece 140. More specifically, the mobile device 121 includes a processor running a software application that facilitates communications with the mouthpiece 140. The mobile device 121 can be, for example, a mobile phone, a portable digital assistant (PDA), or a laptop. The mobile device 121 can communicate with the mouthpiece 140 by a wireless or wired connection. During operation, a patient activates the neurostimulation system 100 via the mobile device 121. After activation, the patient can start an NINM treatment session, stop the NINM treatment session, or pause the NINM treatment session by manipulating the mobile device 121. During an NINM treatment session, the patient engages in an exercise or activity designed to provide neurorehabilitation. For example, during an NINM treatment session, the patient can engage in a physical exercise, a mental exercise, or a cognitive exercise.

Figure 3A:
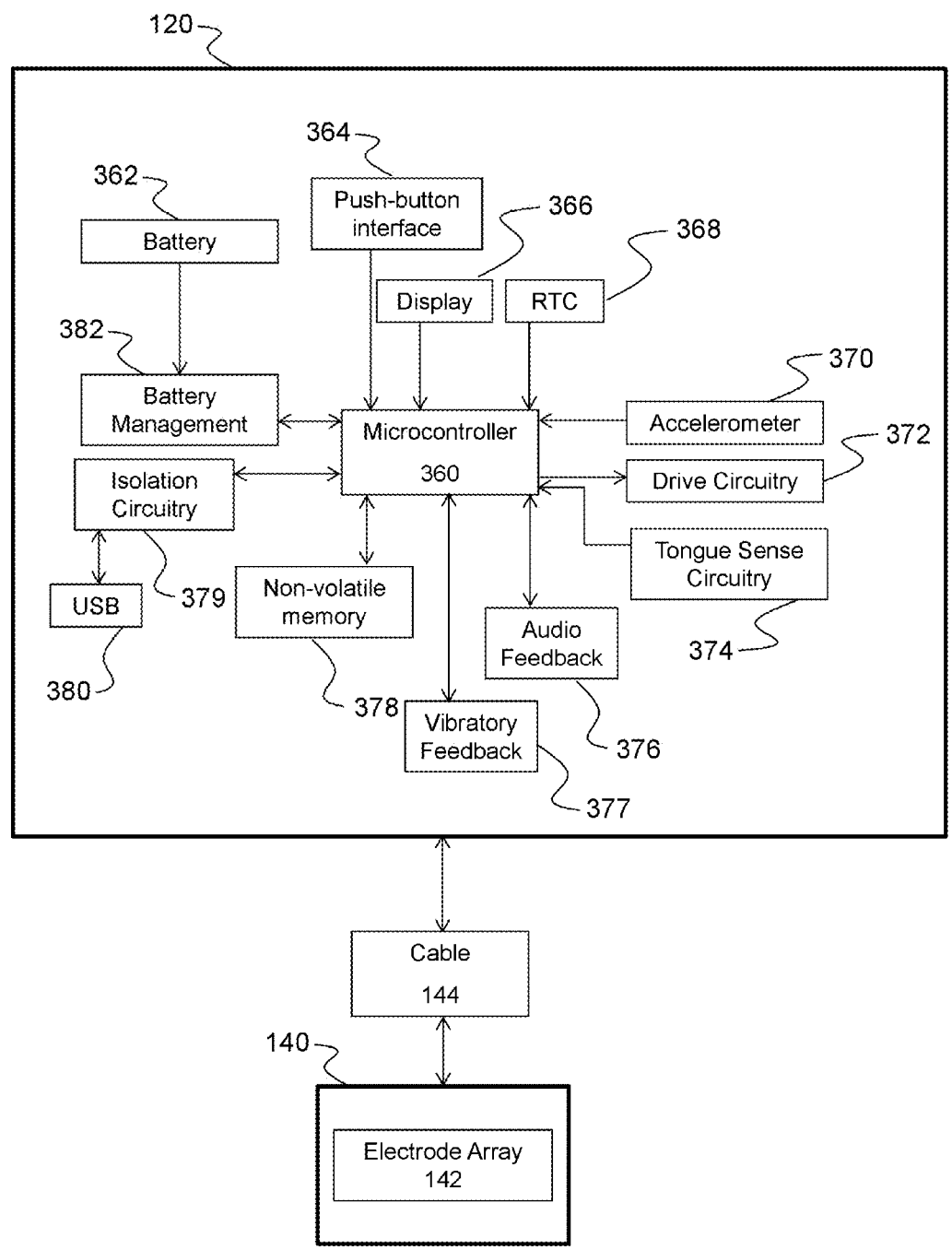
FIG. 3A is a diagram showing a more detailed view of the neurostimulation system depicted in FIGS. 2A and 2B.

FIG. 3A shows the internal circuitry housed within the controller 120. The circuitry includes a microcontroller 360, isolation circuitry 379, a universal serial bus (USB) connection 380, a battery management controller 382, a battery 362, a push-button interface 364, a display 366, a real time clock 368, an accelerometer 370, drive circuitry 372, tongue sense circuitry 374, audio feedback circuitry 376, vibratory feedback circuitry 377, and a non-volatile memory 378. The drive circuitry 372 includes a multiplexor, and an array of resistors to control voltages delivered to the electrode array 142. The microcontroller 360 is in electrical communication with each of the components shown in FIG. 3A. The isolation circuitry 379 provides electrical isolation between the USB connection 380 and all other components included in the controller 120. Additionally, the circuitry shown in FIG. 3A is in communication with the mouthpiece 140 via the external cable 144. During operation, the microcontroller 360 receives electrical power from battery 362 and can store and retrieve information from the non-volatile memory 378. The battery can be charged via the USB connection 380. The battery management circuitry controls the charging of the battery 362. A patient can interact with the controller 120 via the push-button interface 122 that converts the patient's pressing of a button (e.g. an info button, a power button, an intensity-up button, an intensity-down button, and a start/stop button) into an electrical signal that is transmitted to the microcontroller 360. For example, a therapy session can be started when the patient presses a start/stop button after powering on the controller 120. During the therapy session, the drive circuitry 372 provides an electrical signal to the mouthpiece 140 via the cable 144. The electrical signal is communicated to the patient's intraoral cavity via the electrode array 142. The accelerometer 370 can be used to provide information about the patient's motion during the therapy session. Information provided by the accelerometer 370 can be stored in the non-volatile memory 378 at a coarse or detailed level. For example, a therapy session aggregate motion index can be stored based on the number of instances where acceleration rises above a predefined threshold, with or without low pass filtering. Alternatively, acceleration readings could be stored at a predefined sampling interval. The information provided by the accelerometer 370 can be used to determine if the patient is engaged in a physical activity. Based on the information received from the accelerometer 370, the microcontroller 360 can determine an activity level of the patient during a therapy session. For example, if the patient engages in a physical activity for 30 minutes during a therapy session, the accelerometer 370 can periodically communicate (e.g. once every second) to the microcontroller 360 that the sensed motion is larger than a predetermined threshold (e.g. greater than 1 m/s$^2$). In some embodiments, the accelerometer data is stored in the non-volatile memory 378 during the therapy session and transmitted to the mobile device 121 after the therapy session has ended. After the therapy session has ended, the microcontroller 360 can record the amount of time during the therapy session in which the patient was active. In some embodiments, the recorded information can include other data about the therapy session (e.g., the date and time of the session start, the average intensity of electrical neurostimulation delivered to the patient during the session, the average activity level of the patient during the session, the total session time the mouthpiece has been in the patient's mouth, the total session pause time, the number of session shorting events, and/or the length of the session or the type of exercise or activity performed during the therapy session) and can be transmitted to a mobile device. A session shorting event can occur if the current transmitted from the drive circuitry to the electrode array 142 exceeds a predetermined threshold or if the charge transmitted from the drive circuitry to the electrode array exceeds a predetermined threshold over a predetermined time interval. After a session shorting event has occurred, the patient must manually press a pushbutton to resume the therapy session. The real time clock (RTC) 368 provides time and date information to the microcontroller 360. In some embodiments, the controller 120 is authorized by a physician for a predetermined period of time (e.g., two weeks). The RTC 368 periodically communicates date and time information to the microcontroller 360. In some embodiments, the RTC 368 is integrated with the microcontroller. In some embodiments, the RTC 368 is powered by the battery 362, and upon failure of the battery 362, the RTC 368 is powered by a backup battery. After the predetermined period of time has elapsed, the controller 120 can no longer initiate the delivery of electrical signals to the mouthpiece 140 and the patient must visit the physician to reauthorize use of the controller 120. The display 366 displays information received by the microcontroller 360 to the patient. For example, the display 366 can display the time of day, therapy information, battery information, time remaining in a therapy session, error information, and the status of the controller 120. The audio feedback circuitry 376 and vibratory feedback circuitry 377 can give feedback to a user when the device changes state. For example, when a therapy session begins, the audio feedback circuitry 376 and the vibratory feedback circuitry 377 can provide auditory and/or vibratory cues to the patient, notifying the patient that the therapy session has been initiated. Other possible state changes that may trigger audio and/or vibratory cues include pausing a therapy session, resuming a therapy session, the end of a timed session, canceling a timed session, or error messaging. In some embodiments, a clinician can turn off one or more of the auditory or vibratory cues to tailor the feedback to an individual patient's needs. The tongue sense circuitry 374 measures the current passing from the drive circuitry to the electrode array 142. Upon sensing a current above a predetermined threshold, the tongue sense circuitry 374 presents a high digital signal to the microcontroller 360, indicating that the tongue is in contact with the electrode array 142. If the current is below the predetermined threshold, the tongue sense circuitry 374 presents a low digital signal to the microcontroller 360, indicating that the tongue is not in contact or is in partial contact with the electrode array 142. The indications received from the tongue sense circuitry 374 can be stored in the non-volatile memory 378. In some embodiments, the display 366 can be an organic light emitting diode (OLED) display. In some embodiments, the display 366 can be a liquid crystal display (LCD). In some embodiments, a display 366 is not included with the controller 120. In some embodiments, neither the controller 120 nor the mouthpiece 140 includes a cable, and the controller 120 communicates wirelessly with the mouthpiece 140. In some embodiments, neither the controller 120 nor the mouthpiece 140 includes an accelerometer. In some embodiments, the drive circuitry 372 is located within the mouthpiece. In some embodiments, a portion of the drive circuitry 372 is located within the mouthpiece 140 and a portion of the drive circuitry 372 is located within the controller 120. In some embodiments, neither the controller 120 nor the mouthpiece 140 includes tongue sense circuitry 374. In some embodiments, the mouthpiece 140 includes a microcontroller and a multiplexer.

Figure 3B:
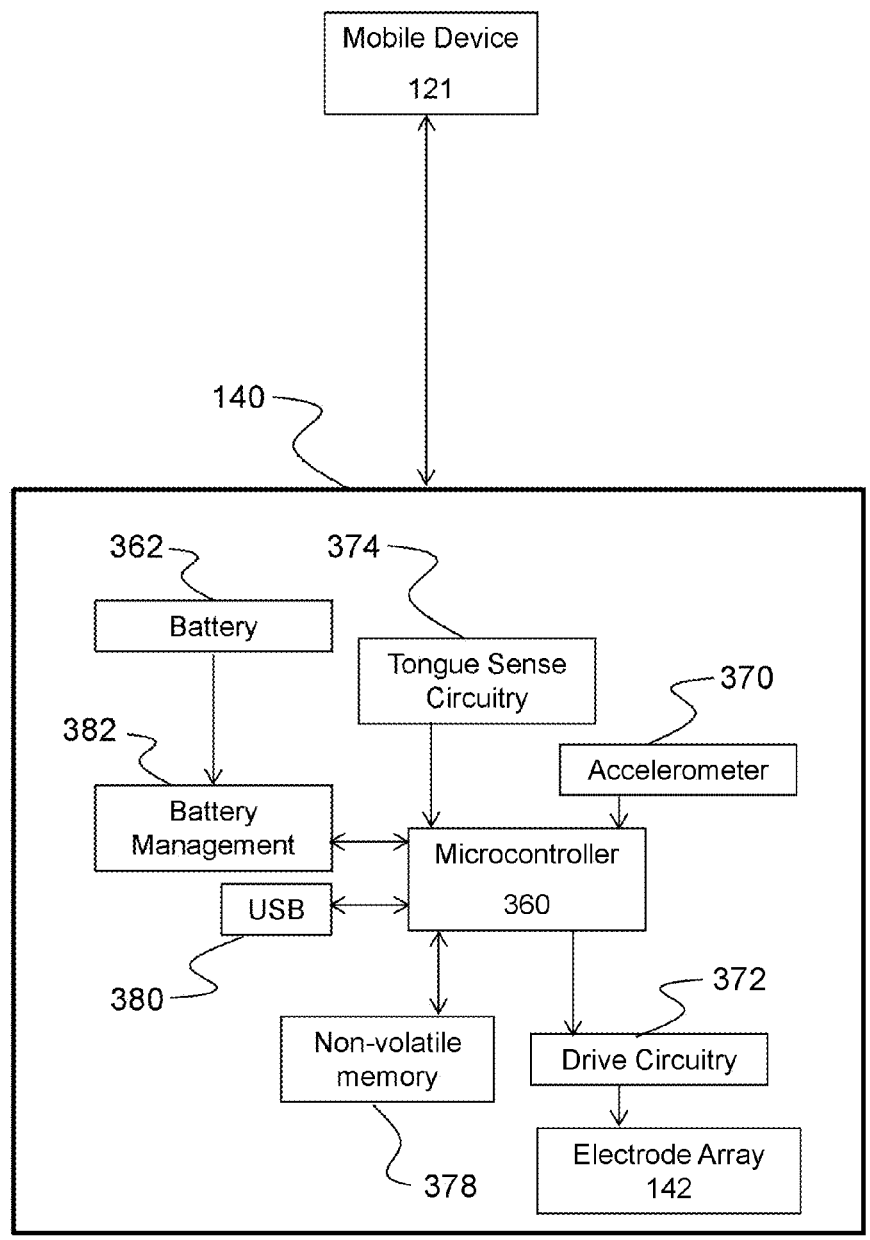
FIG. 3B is a diagram showing a more detailed view of the neurostimulation system depicted in FIG. 2C.

FIG. 3B shows a more detailed view of FIG. 2C. The mouthpiece 140 includes a battery 362, tongue sense circuitry 374, an accelerometer 370, a microcontroller 360, drive circuitry 372, a non-volatile memory 378, a universal serial bus controller (USB) 380, and battery management circuitry 382. During operation, the microcontroller receives electrical power from battery 362 and can store and retrieve information from the non-volatile memory 378. The battery can be charged via the USB connection 380.

The battery management circuitry 382 controls the charging of the battery 362. A patient can interact with the mouthpiece 140 via the mobile device 121. The mobile device 121 includes an application (e.g. software running on a processor) that allows the patient to control the mouthpiece 140. For example, the application can include an info button, a power button an intensity-up button, an intensity-down button, and a start/stop button that are presented to the user visually via the mobile device 121. When the patient presses a button presented by the application running on the mobile device 121, a signal is transmitted to the microcontroller 360 housed within the mouthpiece 140. For example, a therapy session can be started when the patient presses a start/stop button on the mobile device 121. During the therapy session, the drive circuitry 372 provides an electrical signal to an electrode array 142 located on the mouthpiece 140. The accelerometer 370 can be used to provide information about the patient's motion during the therapy session. The information provided by the accelerometer 370 can be used to determine if the patient is engaged in a physical activity. Based on the information received from the accelerometer 370, the microcontroller 360 can determine an activity level of the patient during a therapy session. For example, if the patient engages in a physical activity for 30 minutes during a therapy session, the accelerometer 370 can periodically communicate (e.g. once every second) to the microcontroller 360 that the sensed motion is larger than a predetermined threshold (e.g. greater than 1 m/s$^2$). After the therapy session has ended, the microcontroller 360 can record the amount of time during the therapy session in which the patient was active. In some embodiments, the accelerometer 370 is located within the mobile device 121 and the mobile device 121 determines an activity level of a patient during the therapy session based on information received from the accelerometer 370. The mobile device can then record the amount of time during the therapy session in which the patient was active. The mobile device 121 includes a real time clock (RTC) 368 that provides time and date information to the microcontroller 360. In some embodiments, the mouthpiece 140 is authorized by a physician for a predetermined period of time (e.g., two weeks). After the predetermined period of time has elapsed, the mouthpiece 140 can no longer deliver electrical signals to the patient via the electrode array 142 and the patient must visit the physician to reauthorize use of the mouthpiece 140. In some embodiments, the mouthpiece 140 includes pushbuttons (e.g., an on/off button) and a patient can manually operate the mouthpiece 140 via the pushbuttons. After a therapy session, the mouthpiece 140 can transmit information about the therapy session to a mobile device. In some embodiments, the mouthpiece 140 does not include a USB controller 380 and instead communicates only via wireless communications with the controller.

Figure 3C:
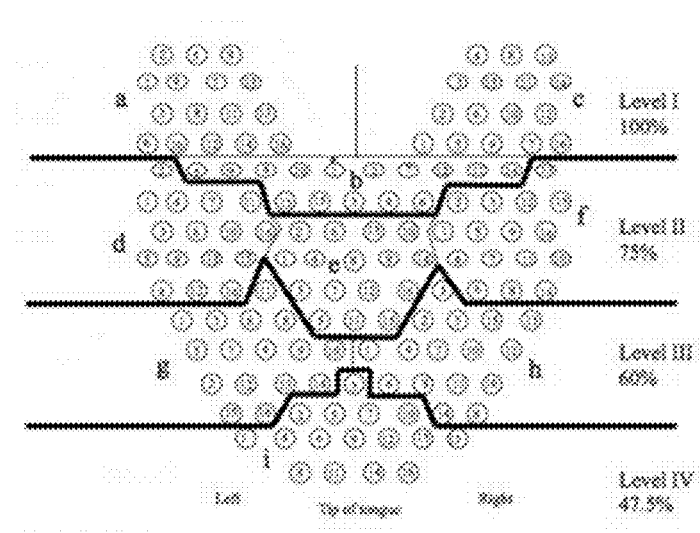
FIG. 3C is a diagram showing a more detailed view of an electrode array.

FIG. 3C shows a more detailed view of the electrode array 142. The electrode array 142 can be separated into 9 groups of electrodes, labelled a-i, with each group having 16 electrodes, except group b which has 15 electrodes. Each electrode within the group corresponds to one of 16 electrical channels. During operation, the drive circuitry can deliver a sequence of electrical pulses to the electrode array 142 to provide neurostimulation of at least one of the patient's trigeminal or facial nerve. The electrical pulse amplitude delivered to each group of electrodes can be larger near a posterior portion of the tongue and smaller at an anterior portion of the tongue. For example, the pulse amplitude of electrical signals delivered to groups a-c can be 19 volts or 100% of a maximum value, the pulse amplitude of electrical signals delivered to groups d-f can be 14.25 volts or 75% of the maximum value, the pulse amplitude of electrical signals delivered to groups g-h can be 11.4 volts or 60% of the maximum value, and the pulse amplitude of electrical signals delivered to group i can be 9.025 volts or 47.5% of the maximum value. In some embodiments, the maximum voltage is in the range of 0 to 40 volts. The pulses delivered to the patient by the electrode array 142 can be random or repeating. The location of pulses can be varied across the electrode array 142 such that different electrodes are active at different times, and the duration and/or intensity of pulses may vary from electrode. For oral tissue stimulation, currents of 0.5-50 mA and voltages of 1-40 volts can be used. In some embodiments, transient currents can be larger than 50 mA. The stimulus waveform may have a variety of time-dependent forms, and for cutaneous electrical stimulation, pulse trains and bursts of pulses can be used. Where continuously supplied, pulses may be 1-500 microseconds long and repeat at rates from 1-1000 pulses/second. Where supplied in bursts, pulses may be grouped into bursts of 1-100 pulses/burst, with a burst rate of 1-100 bursts/second.

Figure 3D:
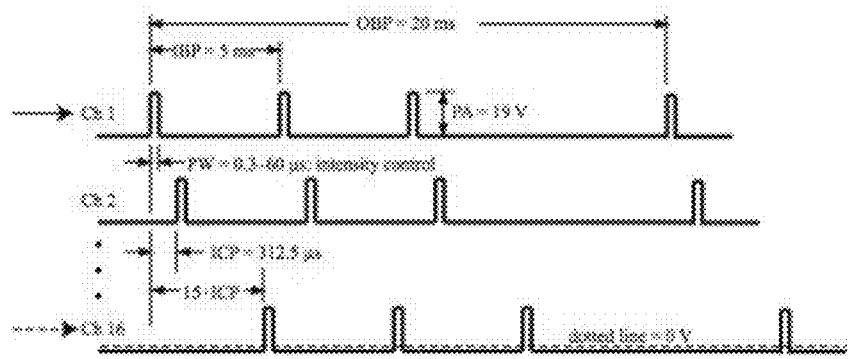
FIG. 3D is a graph showing an exemplary sequence of pulses for effecting neurostimulation of a patient.

In some embodiments, pulsed waveforms are delivered to the electrode array 142. FIG. 3D shows an exemplary sequence of pulses that can be delivered to the electrode array 142 by the drive circuitry 372. A burst of three pulses, each spaced apart by 5 ms is delivered to each of the 16 channels. The pulses in neighboring channels are offset from one another by 312.5 µs. The burst of pulses repeats every 20 ms. The width of each pulse can be varied from 0.3-60 µs to control an intensity of neurostimulation (e.g., a pulse having a width of 0.3 µs will cause a smaller amount of neurostimulation than a pulse having a width of 60 µs).

FIG. 4A shows a method of operation 400 of a controller 120 as described in FIGS. 2A, 2B and 3A. A patient attaches a mouthpiece 140 to a controller 120 (step 404). The patient turns on the controller 120 (step 408) using, for example, a power button. The patient places the controller 120 around his/her neck (step 412) as shown in FIG. 1B. The patient places a mouthpiece 140 in his/her mouth (step 416). The patient initiates a therapy session by pressing a start/stop button (step 420). During the therapy session, the controller 120 delivers electrical signals to the mouthpiece 140. The patient calibrates the intensity of the electrical signals (step 424). The patient raises the intensity of the electrical signals delivered to the mouthpiece by pressing an intensity-up button until the neurostimulation is above the patient's sensitivity level. The patient presses an intensity-down button until the neurostimulation is comfortable and non-painful. After the calibration step, the patient performs a prescribed exercise (step 428). The exercise can be cognitive, mental, or physical. In some embodiments, physical exercise includes the patient attempting to maintain a normal posture or gait, the patient moving his/her limbs, or the patient undergoing speech exercises. Cognitive exercises can include "brain training" exercises, typically computerized, that are designed to require the use of attention span, memory, or reading comprehension. Mental exercises can include visualization exercises, meditation, relaxation techniques, and progressive exposure to "triggers" for compulsive behaviors.

In some embodiments, the patient can rest for a period of time during the therapy session (e.g. the patient can rest for 2 minutes during a 30 minute therapy session). After a predetermined period of time (for example, thirty minutes) has elapsed, the therapy session ends (step 432) and the controller 120 stops delivering electrical signals to the mouthpiece 140. In some embodiments, the intensity of electrical signals increases from zero to the last use level selected by the patient over a time duration in the range of 1-5 seconds after the patient starts a therapy session by pressing the start/stop button. In some embodiments, the intensity of electrical signals is set to a fraction of the last use level selected by the patient (e.g. ¾ of the last level selected) after the patient starts a therapy session by pressing the start/stop button. In some embodiments, the intensity of electrical signals increases from zero to a fraction of the last use level selected by the patient (e.g. ¾ of the last level selected) over a time duration in the range of 1-5 seconds after the patient starts a therapy session by pressing the start/stop button. In some embodiments, the intensity of electrical signals increases instantaneously from zero to the last use level selected by the patient after the patient starts a therapy session by pressing the start/stop button.

In some embodiments, the mouthpiece 140 is connected to the controller 120 after the controller 120 is turned on. In some embodiments, the mouthpiece 140 is connected to the controller 120 after the controller 120 is donned by the patient. In some embodiments, the patient calibrates the intensity of the electrical signals before initiating a therapy session. In some embodiments, a patient performs an initial calibration of the intensity of electrical signals in the presence of a clinician and does not calibrate the intensity of the electrical signals during subsequent treatments performed in the absence of a clinician.

FIG. 4B shows a method of operation 449 of the non-invasive neurostimulation system 100 described in FIGS. 2C and 3B. A patient activates a mobile device 121 (step 450). The patient places a mouthpiece 140 in his/her mouth (step 454). The patient initiates a therapy session by pressing a start/stop button within an application running on the mobile device 121 (step 458). During the therapy session, circuitry within the mouthpiece 140 delivers electrical signals to an electrode array 142 located on the mouthpiece 140. The patient calibrates the intensity of the electrical signals (step 462). The patient first raises the intensity of the electrical signals delivered to the mouthpiece 140 by pressing an intensity-up button located within an application running on the mobile device 121 until the neurostimulation is above the patient's sensitivity level. The patient presses an intensity-down button running within an application on the mobile device 121 until the neurostimulation is comfortable and non-painful. After the calibration step, the patient performs a prescribed exercise (step 464). The exercise can be cognitive, mental, or physical. In some embodiments, the patient can rest for a period of time during the therapy session (e.g. the patient can rest for 5 minutes during a 30 minute therapy session). After a predetermined period of time (for example, thirty minutes) has elapsed, the therapy session ends (step 468) and the circuitry located within the mouthpiece 140 stops delivering electrical signals to the electrode array 142. In some embodiments, the calibration of the intensity of the electrical signals takes place before the patient initiates a therapy session.

Figure 5A:
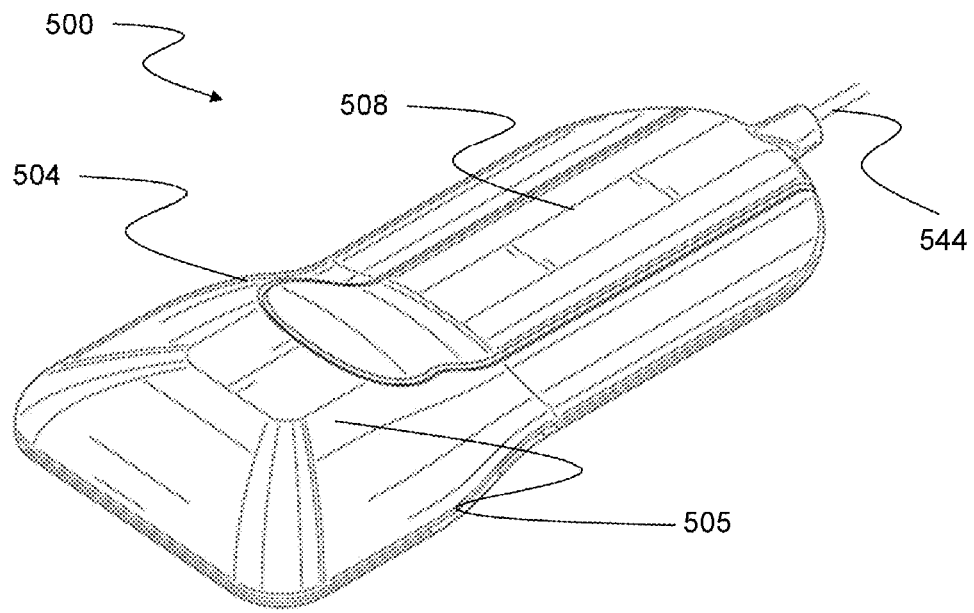
FIG. 5A is a diagram showing an isometric view of a mouthpiece in accordance with an illustrative embodiment of the invention.
Figure 5B:
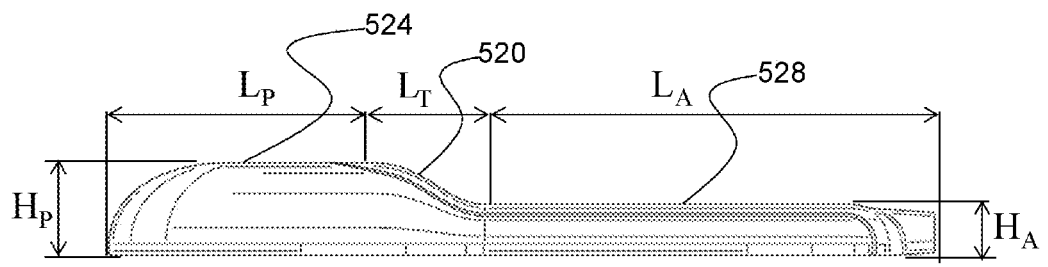
FIG. 5B is a diagram showing a side view of a mouthpiece in accordance with an illustrative embodiment of the invention.
Figure 5C:
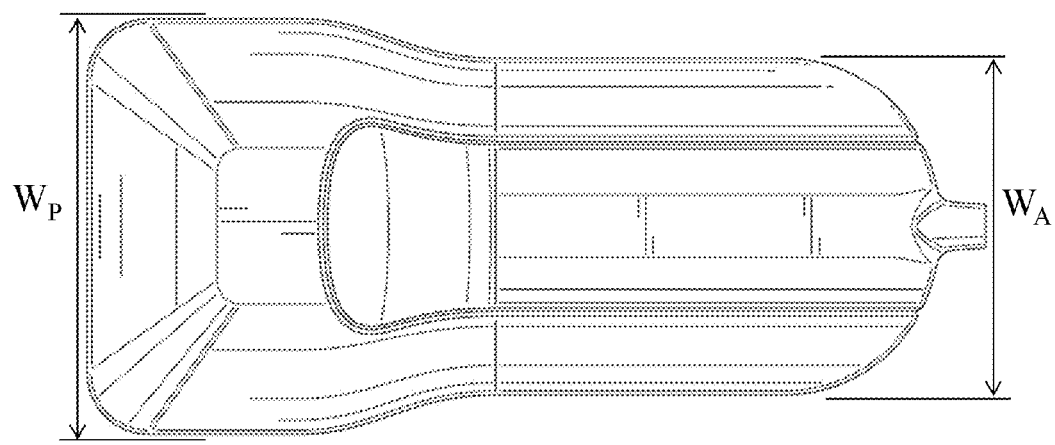
FIG. 5C is a diagram showing a top view of a mouthpiece in accordance with an illustrative embodiment of the invention.
Figure 5D:
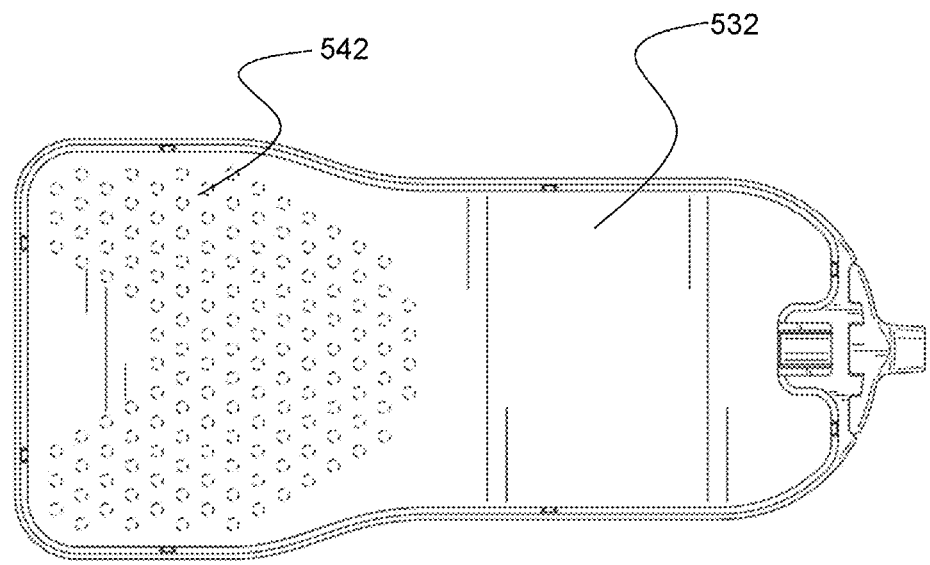
FIG. 5D is a diagram showing a bottom view of a mouthpiece in accordance with an illustrative embodiment of the invention.
Figure 5E:
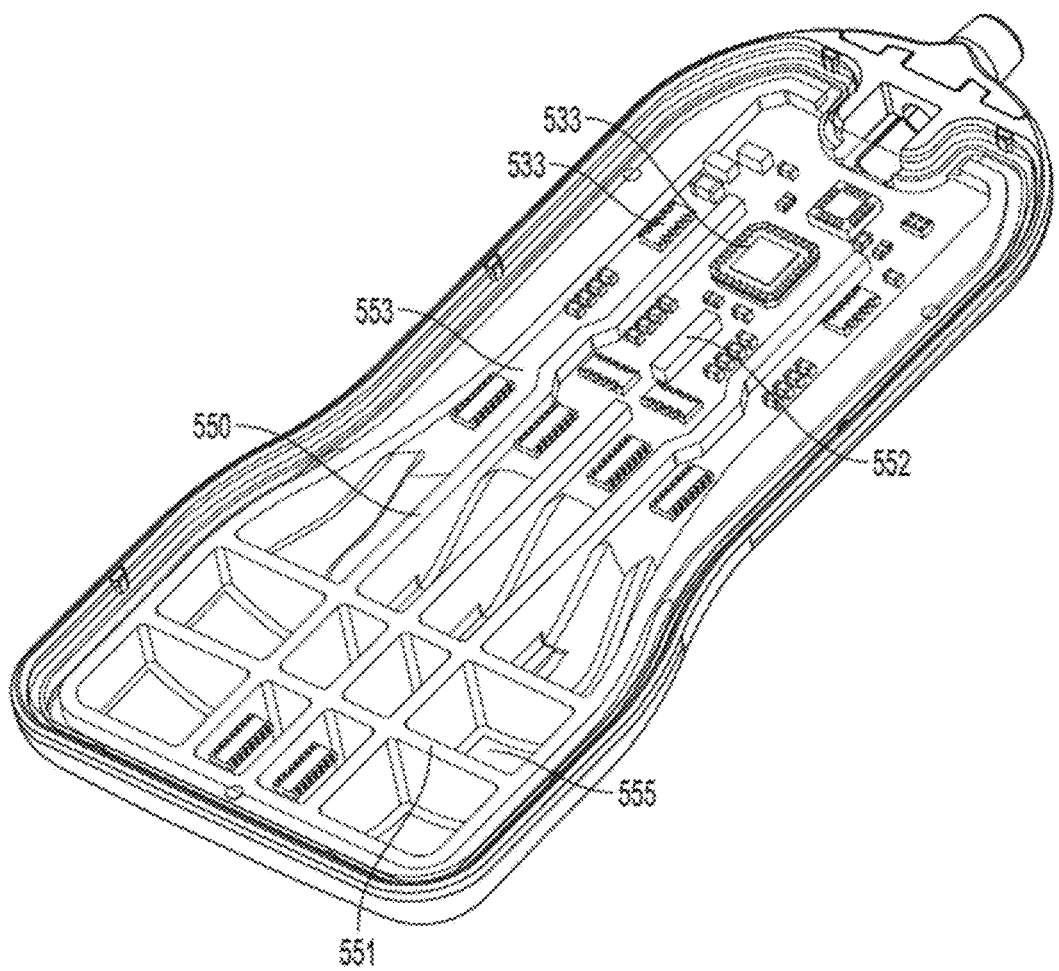
FIGS. 5E and 5F are diagrams showing a bottom view of the mouthpiece in accordance with an illustrative embodiment of the invention.
Figure 5F:
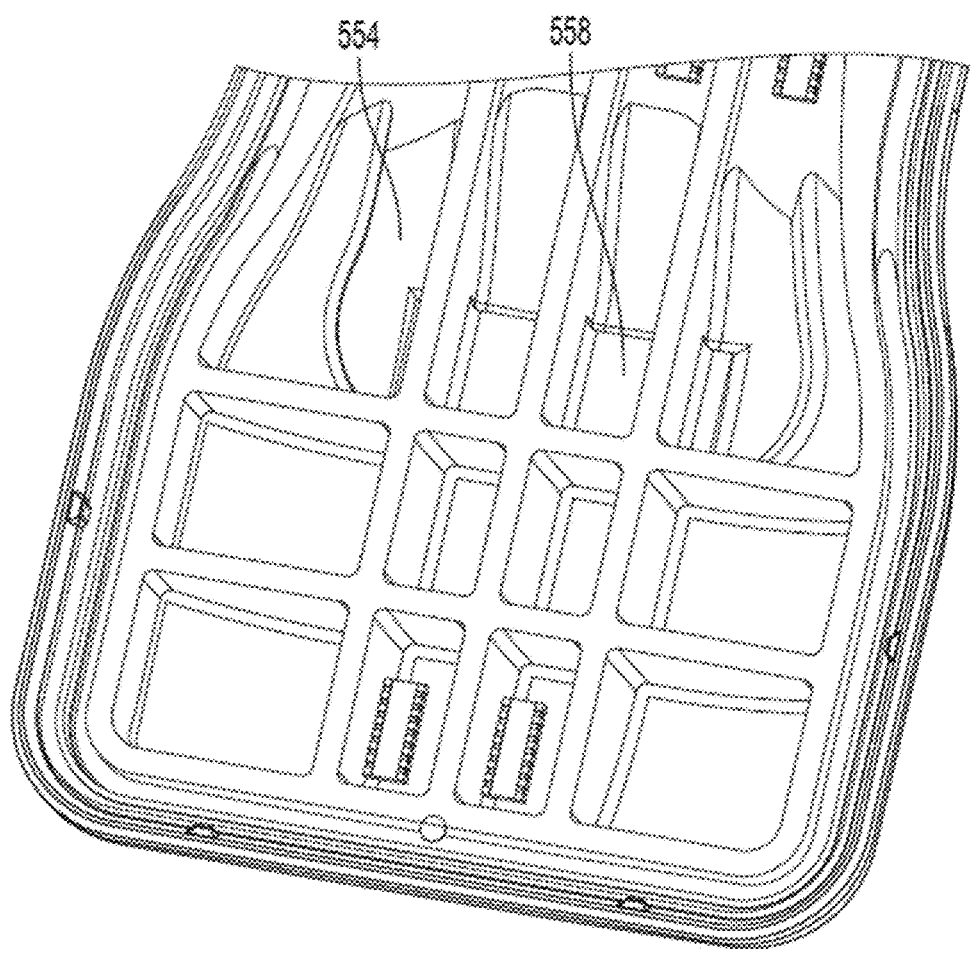

FIGS. 5A-5F show a mouthpiece 500. The mouthpiece 500 includes a housing 504, a spacer 508, a transition region 520, a posterior region 524, an anterior region 528, a printed circuit board 532, internal circuitry 533, an electrode array 542, and a cable 544. The housing 504 includes an outer shell 505, longitudinal ribs 550, transverse ribs 551, columns 552, valleys 553, shoring 554, pockets 555, and a platform 558. The mouthpiece 500 has three regions, a posterior region 524, a transition region 520, and an anterior region 528. The transition region 520 smoothly connects the anterior region 528 with the posterior region 524. The printed circuit board 532 attaches to the bottom side of the housing 504. The internal circuitry 533 is mounted to the top side of the printed circuit board 532 and is covered by the housing 504. The cable 544 is in communication with the internal circuitry 533 and the internal circuitry 533 is in communication with the electrode array 542. The outer shell 505 of the housing 504 has an exemplary thickness in the range of 0.5 to 2 mm. The outer shell can be made of glass filled nylon, nylon, acrylonitrile butadiene styrene (ABS), polycarbonate (PC), polyether ether ketone (PEEK), alloy metal, or metal, having a compression strength in the range of 375 to 590 N. In some embodiments, the outer shell 505 has two different thicknesses. For example, the anterior region of the outer shell 505 can have a thickness in the range of 1.2 to 2 mm and the posterior region can have a thickness in the range of 0.5 to 1.2 mm. The thickness of the outer shell 505 can vary smoothly in the transition region such that there are no discontinuities or steps in the thickness of the outer shell 505. In some embodiments, the thickness of the outer shell 505 in the anterior region is chosen to withstand biting by the patient. In some embodiments, the thickness of the outer shell 505 in the posterior region is selected to provide retention of the mouthpiece 500, thereby preventing accidental ejection of the mouthpiece 500. By itself, the outer shell 505 cannot withstand biting forces from the patient (e.g., the outer shell undergoes significant deflections and/or experiences plastic deformation). The longitudinal ribs 550, transverse ribs 551, columns 552, shoring 554, and platform 558 can provide structural support for the outer shell 505 to prevent damage due to biting by the patient. The longitudinal ribs 550 can extend longitudinally along the housing 504. The longitudinal ribs 550 can be regularly spaced, creating valleys 553 therebetween as shown in FIG. 5E. Internal circuitry 533 can be located in the valleys 553. In an exemplary embodiment, the longitudinal ribs 550 have a width in the range of 0.5 to 2 mm, and a height that varies from approximately 6 mm in the posterior region 524 to 1 mm in the anterior region 528. In some embodiments, the longitudinal ribs are irregularly spaced, with the spacing between ribs being larger towards the perimeter of the outer shell 505 and smaller towards a central portion of the outer shell 505. In some embodiments, the longitudinal ribs are separated by a distance in the range of 4 to 9.0 mm as measured from center to center. The transverse ribs 551 can be located in the posterior region 524 and traverse a width of the housing 504. The transverse ribs can be spaced regularly, as shown in FIG. 5E. In an exemplary embodiment, the transverse ribs 551 have a width of in the range of 0.5 to 1.5 mm, and a height of in the range of 4 to 7 mm. In some embodiments, the transverse ribs 551 can intersect with the longitudinal ribs 550, creating pockets 555 as shown in FIG. 5E. Internal circuitry 533 can be located in the pockets 555. In some embodiments, the transverse ribs are irregularly spaced, with the spacing between ribs being larger towards the perimeter of the outer shell 505 and smaller towards a central portion of the outer shell 505. The column 552 can have a rectangular cross section and be located in an anterior region 528 of the housing 504. In some embodiments, one or more columns 552 are regularly spaced and traverse a width of the housing 504. The columns 552 can provide resistance to compressive forces exerted on the mouthpiece 500, thereby providing protection of the internal circuitry 533. The columns 552 can have a thickness in the range of 0.5 to 2 mm. In some embodiments, the height of the columns 552 is greater than the thickness of the internal circuitry 533, thereby providing a clearance between the internal circuitry 533 and the outer shell 505. In some embodiments, the height of the columns 552 is at least 1 mm greater than the thickness of the internal circuitry 533. In some embodiments, the platform 558 is directly connected to one or more longitudinal ribs and one or more transverse ribs, thereby providing increased capacity to withstand shear and compressive loads. The thickness of the platform 558 can be in the range of 1.5 to 3.5 mm. In some embodiments, the shoring 554 includes a layer of material with a thickness greater than the thickness of the outer shell 505. The thickness of the shoring 554 can be in the range of 0.5 to 2 mm. In some embodiments, the thickness of the outer shell 505 is smaller in the region of the shoring 554 than in other regions to accommodate the spacer 508. For example, the thickness of the outer shell can be 1.5 mm in the anterior and posterior regions and 0.5 mm in the region of the shoring 554. During operation, a patient places a portion of the mouthpiece 500 in his/her mouth to engage in an NINM therapy session. The patient bites down on the mouthpiece 500 with his/her front teeth to secure a position of the mouthpiece. The patient's bottom teeth contact the printed circuit board 532 and the patient's tongue contacts the electrode array 542. In some embodiments, the patient relaxes his/her mouth to secure a position of the mouthpiece. The internal circuitry delivers electrical neurostimulation signals to the patient's tongue via the electrode array 542. In some embodiments, the spacer 508 can provide a soft and comfortable bite surface so that stress is not concentrated at small areas where the patient's teeth contact the mouthpiece 500 during biting. For example, the spacer 508 can be made from thermoplastic polyurethane (TPU), thermoplastic elastomer (TPE), or silicone. In some embodiments, the transverse ribs 551 are located in the anterior region and traverse a width of the housing 504.

Figure 6A:
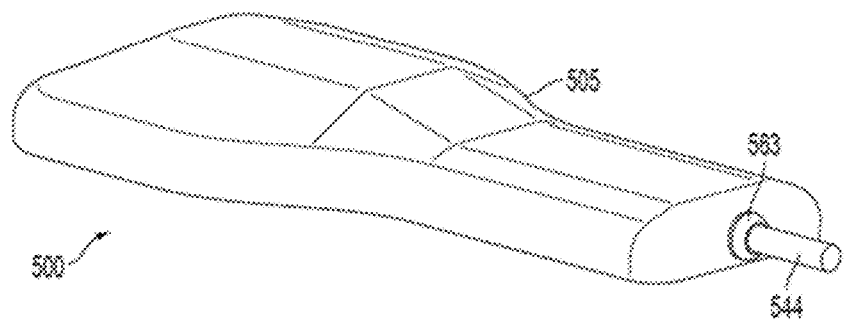
FIG. 6A is a diagram showing an isometric view of a mouthpiece in accordance with an illustrative embodiment of the invention.
Figure 6B:
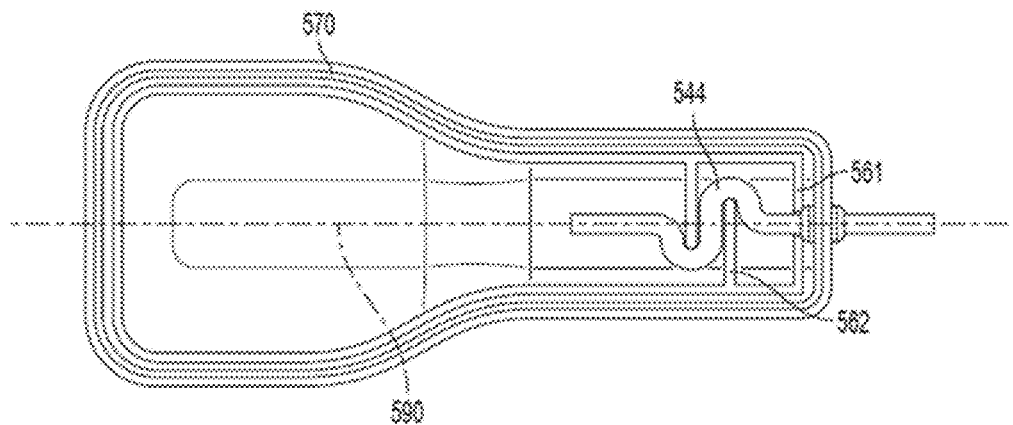
FIG. 6B is a diagram showing a bottom view of the mouthpiece in accordance with an illustrative embodiment of the invention.

FIGS. 6A-6B show a more detailed view of the outer shell 505. The outer shell includes a glue well 570, internal fins 561 and 562, and a central longitudinal axis 590. The internal fins include at least one pair of entrance fins 561. The entrance fins 561 can be symmetric about the longitudinal axis 590 and can guide the cable 544 along the longitudinal axis 590 without causing substantial bending thereof. A glue, adhesive, or epoxy can provide a rigid mechanical connection between the cable 544 and the entrance fins 561. For example, the glue, adhesive, or epoxy can be a UV cured adhesive, or cyanoacrylate. The internal fins also in include an even number of guiding fins 562. In some embodiments, the internal fins include an odd number of guiding fins 562. For example, the internal fins can include three guiding fins. In some embodiments, the guiding fins 562 are not symmetric about the longitudinal axis 590, with each guiding fin 562 causing an approximately 90 degree bend in the cable 544, and each bend having a radius of curvature approximately equal to two diameters of the cable 544. In some embodiment, each guiding fin 562 causes a bend in the cable 544 of greater than 90 degrees, but less than 180 degrees. The guiding fins 562 are in mechanical contact with the cable 544 and provide frictional resistance that compensates for any tensile strain applied to the cable, for example due to longitudinal forces applied along the cable 544. In some embodiments, the guiding fins 562 provide frictional resistance of at least 100 Newtons. In some embodiments, the guiding fins provide frictional resistance greater than the weight of the mouthpiece. In some embodiments, the guiding fins provide frictional resistance greater than the forces required to disconnect the mouthpiece 140 from the controller 120. In some embodiments, a rubber grommet 563 provides an elastic mechanical attachment between the outer shell 505 and the cable 544 with the outer shell 505 providing a resistance that counteracts any bending strain applied to the cable 544 (e.g., the patient may accidentally pull or tug on the cable while the mouthpiece 500 is secured within the patient's mouth). In some embodiments, the spacer 508 includes an elastomeric element that provides a mechanical connection between the cable 544 and the entrance fins 561. The elastomeric element provides a frictional force that provides a frictional resistance that counteracts any bending stress applied to the cable 544. In some embodiments, the cable 544 can exit the outer shell at a 90 degree angle and be attached to the outer shell by an epoxy, the epoxy providing mechanical resistance of up to 100 Newtons to accommodate bending strains induced by the patient. In some embodiments, the cable 544 is attached to the outer shell by an adhesive or glue. In some embodiments, the cable 544 can exit the outer shell at a 90 degree angle and be mechanically attached to the outer shell by a right-angled elastomeric element, the right-angled elastomeric element interlocking with the outer shell and providing mechanical resistance of up to 100 Newtons to accommodate both bending and tensile strains induced by the patient.

Figure 6C:
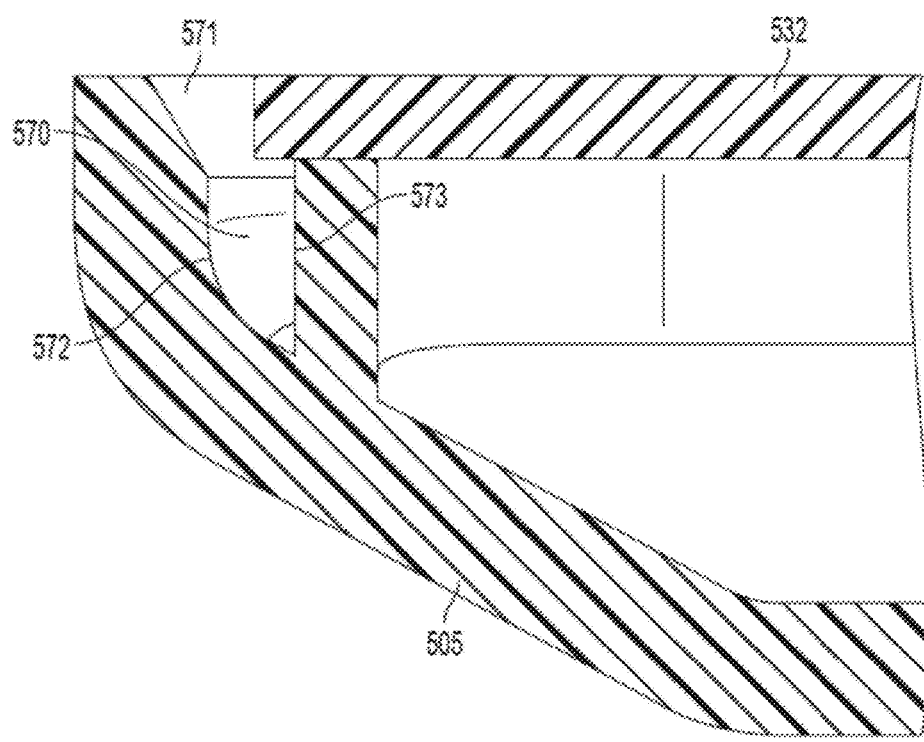
FIG. 6C is a diagram showing a glue well in accordance with an illustrative embodiment of the invention.

FIG. 6C shows a more detailed cross sectional view of the glue well 570. The glue well 570 is located along an outer boundary of the outer shell 505 and accommodates an adhesive (e.g., a biomedical compatible epoxy or glue) that provides a mechanical connection between the printed circuit board 532 and the outer shell 505. The glue well 570 includes a beveled lip 571, and a discontinuously connected cross-section that includes a concave portion 572 and a vertical portion 573 that intersect to form a lowest point of the glue well 570. In some embodiments, the shape of the glue well can be trapezoidal. In some embodiments, the shape of the glue well can be wedged. In some embodiments, the shape of the glue well can be triangular. In some embodiments, the shape of the glue well can be rectangular. In some embodiments, a portion of the glue well can overhang the printed circuit board 532, thereby protecting portions of the printed circuit board from the teeth of the patient. In some embodiments, the adhesive is in contact with the outer shell 505 and the top of the printed circuit board 532. In some embodiments, the adhesive is in contact with the outer shell 505 and the top and side portions of the printed circuit board 532. In some embodiments, the glue well is shaped such that the adhesive is in contact with the outer shell 505 and the side portions of the printed circuit board 532, but only has negligible contact with the top portion of the printed circuit board 532 (e.g., the glue well can have a width greater than a depth).

Figure 6D:
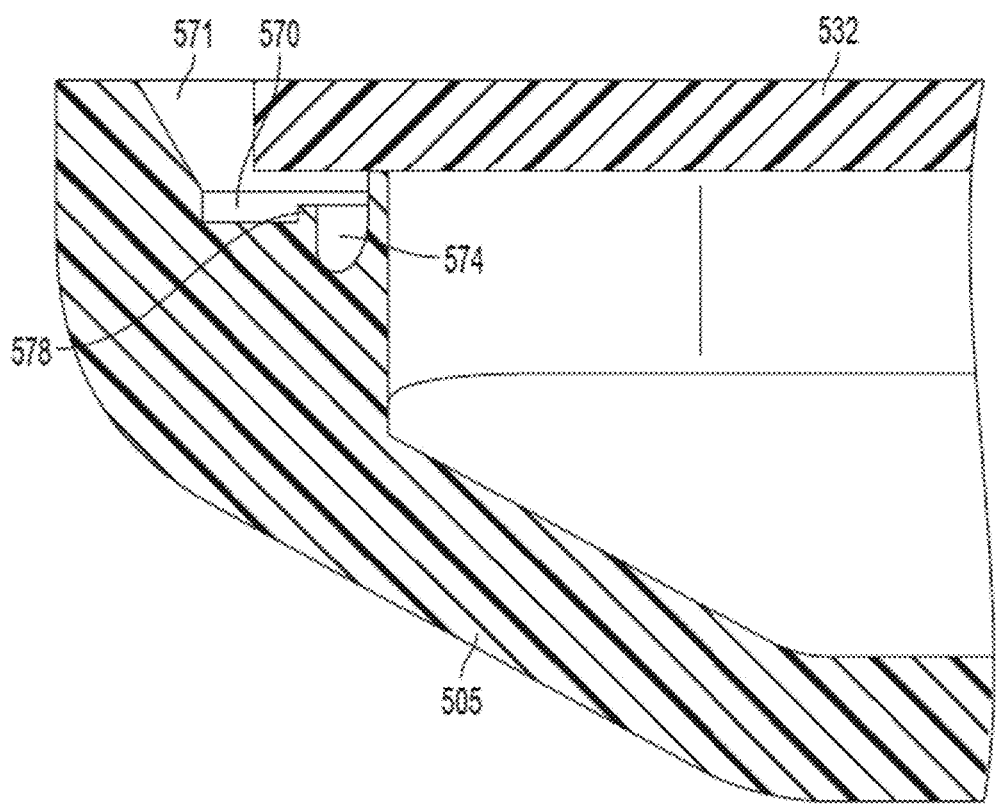
FIG. 6D is a diagram showing a glue well in accordance with an illustrative embodiment of the invention.

FIG. 6D shows an embodiment where the outer shell 505 includes two glue wells, 570 and 574. A first glue well 570 and a second glue well 574 are located along an outer boundary of the outer shell 505 and accommodate an adhesive (e.g., a biomedical compatible epoxy) that provides a mechanical connection between the printed circuit board 532 and the outer shell 505. The second glue well 574 is designed to accommodate a glue or adhesive that overflows from the first glue well 570, thereby preventing glue or adhesive from overflowing onto the bottom side of the printed circuit board. A step 578 is positioned between the first and second glue well to define the height of the first glue well.

Figure 7A:
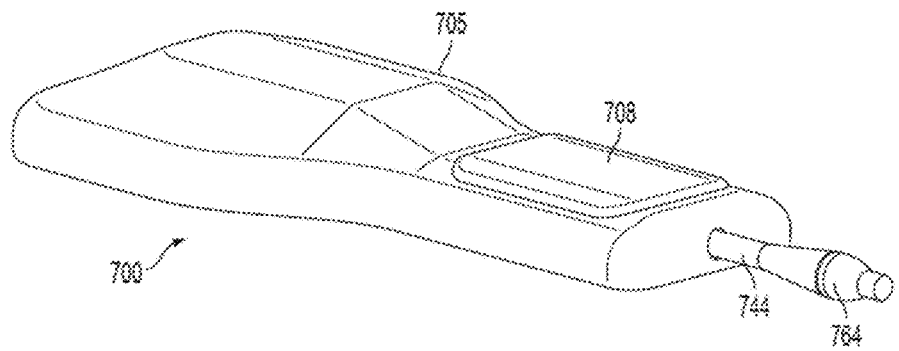
FIG. 7A is a diagram showing an isometric view of a mouthpiece in accordance with an illustrative embodiment of the invention.
Figure 7B:
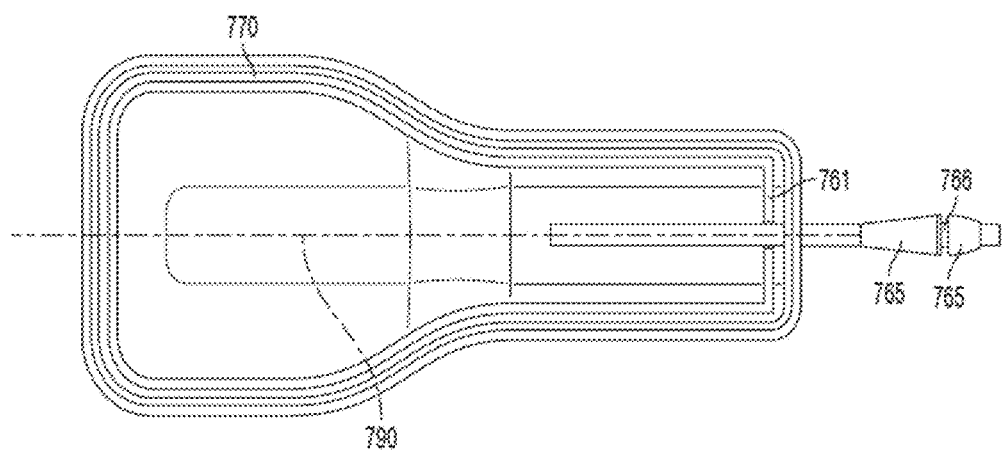
FIG. 7B is a diagram showing a bottom view of the mouthpiece in accordance with an illustrative embodiment of the invention.
Figure 7C:
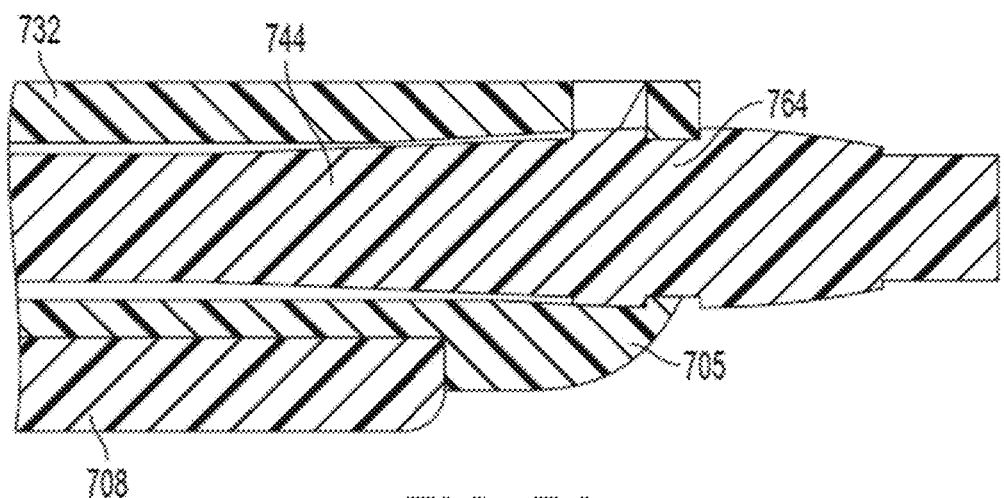
FIG. 7C is a diagram showing a sectional view of the mouthpiece in accordance with an illustrative embodiment of the invention.

FIGS. 7A-7C show a mouthpiece 700. The mouthpiece 700 includes an outer shell 705 having a central longitudinal axis 790, a spacer 708, a cable 744, a sleeve 764, exit fins 761, a glue well 770. The sleeve 764 is integrated with the cable 744 and mechanically couples the cable 744 with the outer shell 705. The sleeve 764 includes two tapered outer portions 765 and a gap 766 separating the two tapered outer portions.

The cable 744 can be pulled towards the outer shell 705 until the gap 766 is aligned with an outer boundary of the mouthpiece 700. Once aligned with the outer shell 705, the sleeve 764 provides a mechanical resistance of up to 100 Newtons to counteract both tensile and bending stresses applied to the cable 744. The cable 744 may additionally be clamped between the printed circuit board 732 and the outer shell 705 as shown in FIG. 7C. The additional clamping can provide additional mechanical resistance to tensile stresses applied to the cable 744.

Figure 8A:
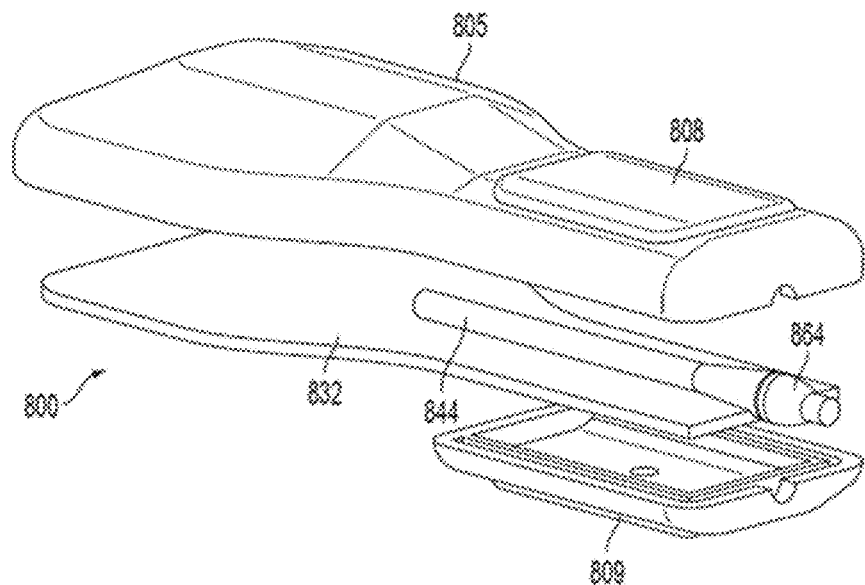
FIGS. 8A and 8B are diagrams showing an isometric view of a mouthpiece in accordance with an illustrative embodiment of the invention.
Figure 8B:
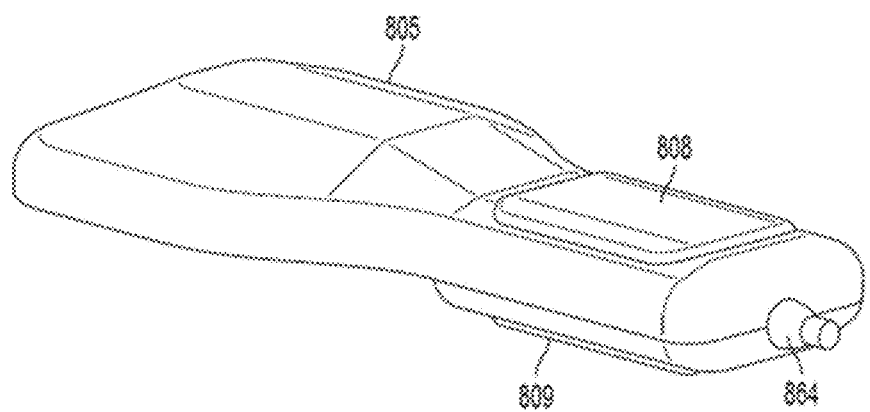
Figure 8C:
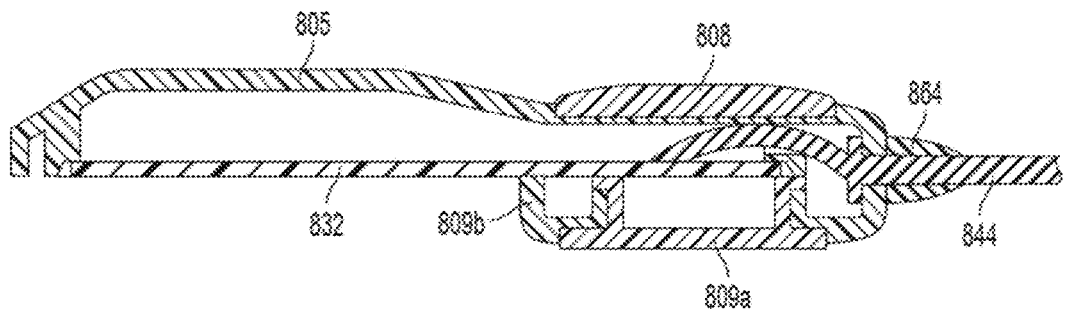
FIG. 8C is a diagram showing a sectional view of the mouthpiece in accordance with an illustrative embodiment of the invention.
Figure 8D:
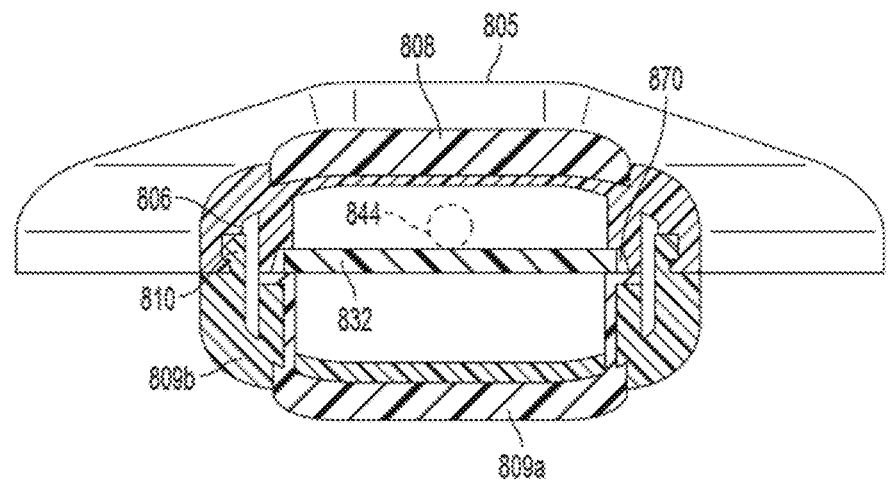
FIG. 8D is a diagram showing a sectional view of the mouthpiece in accordance with an illustrative embodiment of the invention.

FIGS. 8A-8D show a mouthpiece 800. The mouthpiece 800 includes an outer shell 805, a spacer 808, a printed circuit board 832, a cable 844, a sleeve 864, a glue well 870, and a clamp 809. A posterior portion of the cable 844 is connected to the printed circuit board 832 via solder, ribbon connector, or other mechanical connection. The sleeve 864 is integrated with the cable 844 and mechanically couples the cable 844 with the outer shell 805 and clamp 809. The sleeve 864 is similar to the sleeve 764, having two tapered outer portions and a gap. Instead of being pulled through the outer shell 805 as shown in FIG. 7, the sleeve 864 is secured by a clamp 809 that connects to a bottom portion of the outer shell 805. The clamp 809 mechanically secures the printed circuit board 832 to the outer shell 805 and in addition, secures the sleeve 864 to the outer shell 805. In some embodiments, adhesive or glue is added to the glue well 870 to secure the printed circuit board 832 to the outer shell 805. The sleeve 864 provides mechanical resistance (up to 100 Newtons) to bending stresses and tensile stresses in the cable 844. The clamp 809 includes a rigid plastic portion 809b and an elastomeric portion 809a. The rigid plastic portion 809b provides structural integrity, while the elastomeric portion 809a provides a sealing mechanism. For example, the clamp 809 can be placed into contact with the outer shell 805 as shown in FIG. 8D. A narrow protrusion 810 extends from the rigid plastic portion 809b of the clamp 809, the narrow protrusion 810 interlocking with a recessed portion 806 of the outer shell 805. The elastomeric portion 809a contacts the outer shell 805, the glue well 870, and the printed circuit board 832, forming an air tight seal. The air tight seal can protect portions of the printed circuit board 832 from moisture. In some embodiments, the clamp 809 is secured to the outer shell 805 by adding an adhesive or glue to the glue well 870 that contacts both the outer shell and the clamp.

Figure 9A:
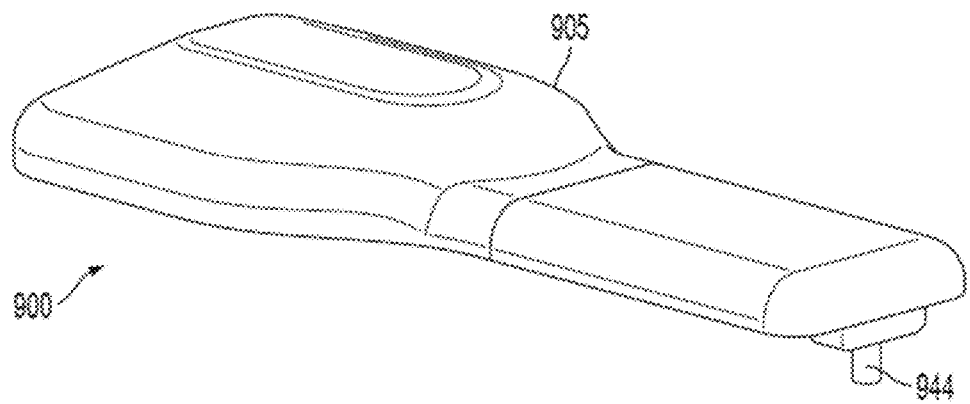
FIGS. 9A and 9B are diagrams showing an isometric view of a mouthpiece in accordance with an illustrative embodiment of the invention.
Figure 9B:
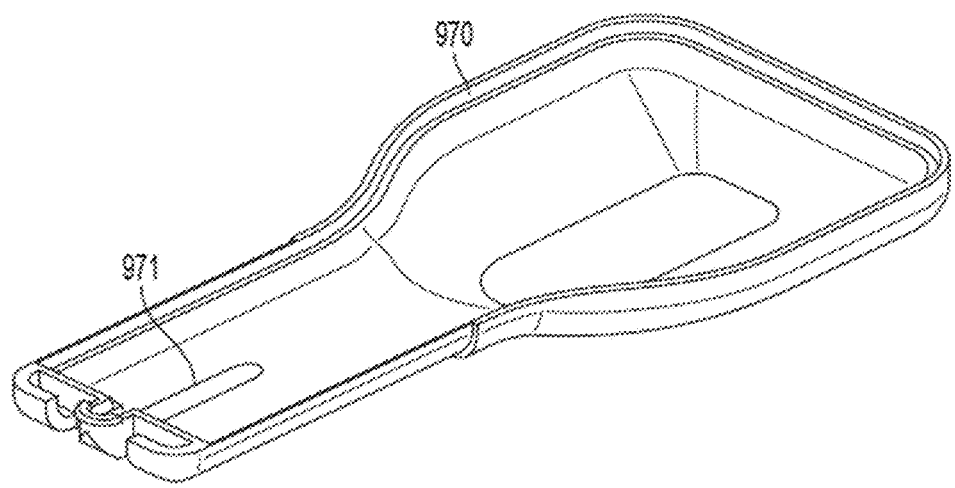
Figure 9C:
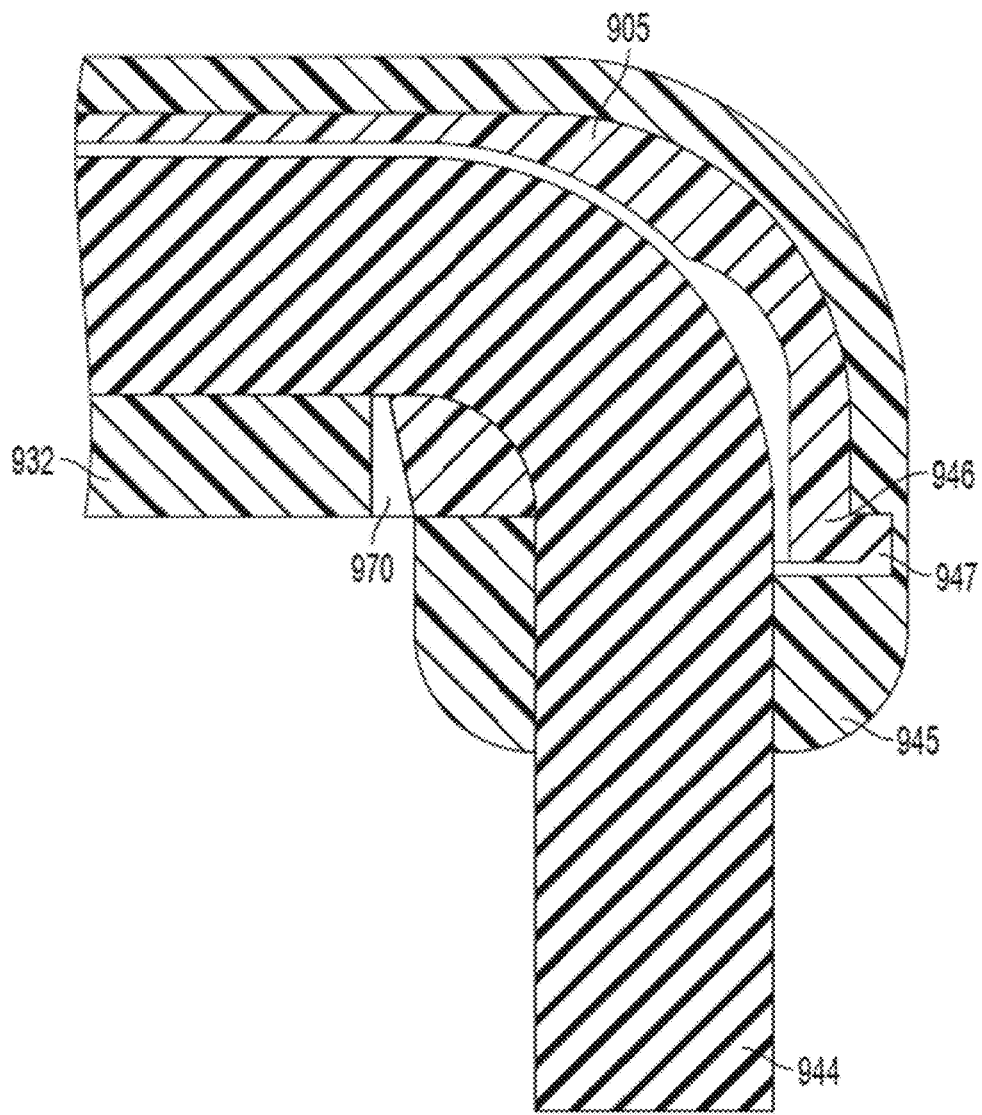
FIG. 9C is a diagram showing a sectional view of the mouthpiece in accordance with an illustrative embodiment of the invention.

FIGS. 9A-9C show a mouthpiece 900. The mouthpiece 900 includes an outer shell 905, a printed circuit board 932, a cable 944, a glue well 970, a boot 945. The outer shell 905 includes a valley 971 and a glue well 970. The valley 971 guides the cable 944 within the outer shell 905, and the glue well 970 accommodates an epoxy or other adhesive to provide a mechanical connection between the printed circuit board 932, the outer shell 905, and the cable 944. The shape of the glue well 970 can be a wedge shape to advantageously provide an interface between the adhesive or epoxy and the printed circuit board 932, the outer shell 905, and the cable 944. A protrusion 946 extends from the outer shell 905 and interlocks with a recessed portion 947 of the boot 945. The interlocked boot 945 is in mechanical contact along an outer diameter of the cable 944 (e.g., the interlocked boot 945 can be in contact with the outer diameter of the cable 944 for a distance in the range of 0.5 to 10 mm). In some embodiments, the interlocked boot 945 can be overmolded, or glued onto the cable 944. In some embodiments, the interlocked boot 945 is mechanically coupled to the cable 944. The interlocked boot 945 can provide mechanical resistance to tugging or pulling (e.g., up to 100 Newtons) of the cable by the patient. In some embodiments, the interlocked boot can provide resistance to both bending strains and tensile strains. In some embodiments, the boot 945 can cover the glue well 970. In some embodiments, the boot 945 can be extended to cover portions of the printed circuit board 932 that are not covered by an electrode array.

Figure 10A:
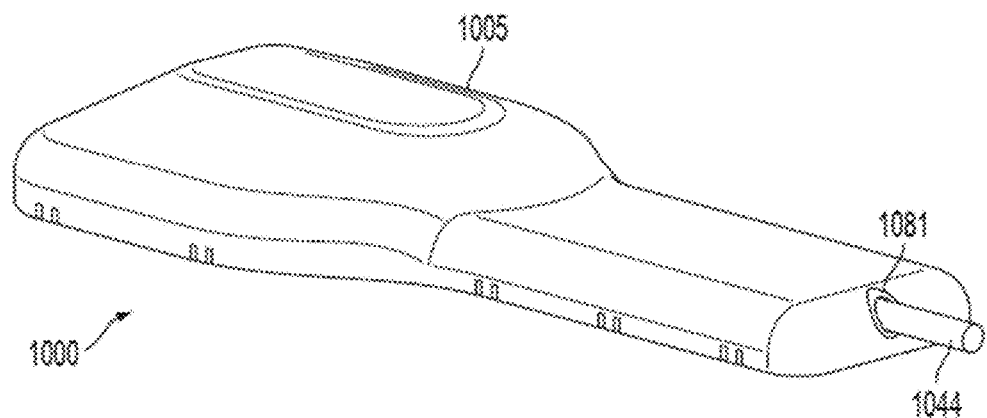
FIGS. 10A and 10B are diagrams showing an isometric view of a mouthpiece in accordance with an illustrative embodiment of the invention.
Figure 10B:
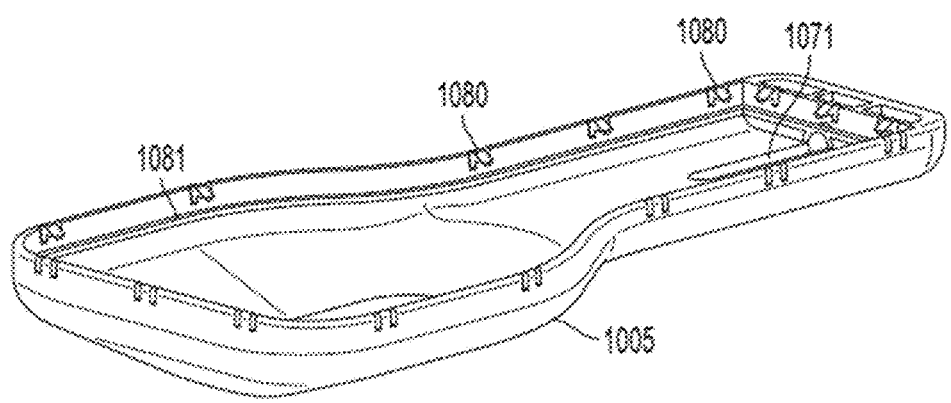
Figure 10C:
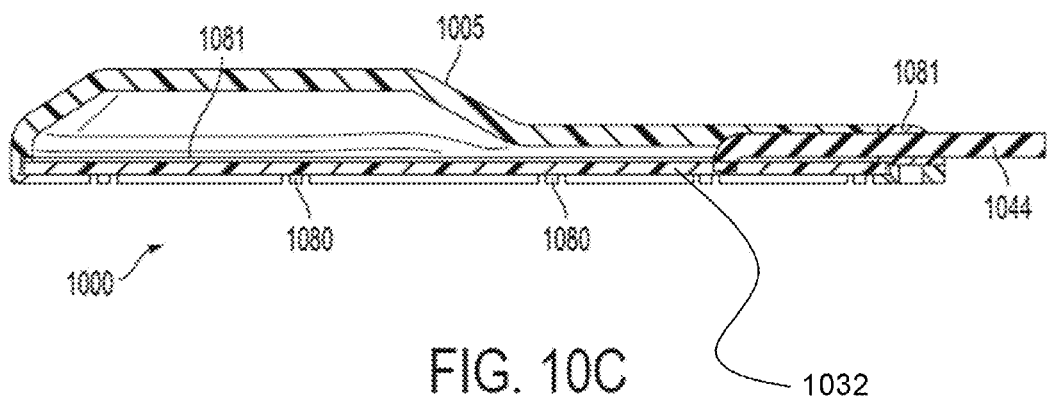
FIG. 10C is a diagram showing a sectional view of the mouthpiece in accordance with an illustrative embodiment of the invention.

FIGS. 10A-10C show a mouthpiece 1000. The mouthpiece 1000 includes an outer shell 1005, a printed circuit board 1032, a cable 1044, a valley 1071, a sealing ring 1081, and clips 1080. Epoxy and/or adhesives are not present in mouthpiece 1000. The printed circuit board 1032 contacts the sealing ring 1081 and is held in place by clips 1080. The clips 1080 can have vertical sidewall and a downward sloping overhang as shown in FIG. 10B. In some embodiments, the clips are spaced along an inner boundary of the outer shell 1005. The cable 1044 is electrically connected to the printed circuit board 1032. Additionally, the sealing ring 1081 forms an aperture at an anterior region of the outer shell 1005, with the cable 1044 passing through the aperture. The valley 1071 guides the cable 1044 from the printed circuit board 1132 to the aperture. The aperture is in contact with the cable 1044 and provides resistance to tugging or pulling of the cable 1044 by the patient. In some embodiments, the aperture can provide resistance to both bending and tensile strains on the cable 1044. In some embodiments, the sealing ring 1081 is composed of a low durometer elastomer such as TPE, TPU, or silicone. In some embodiments, the sealing ring can be replaced by a glue well or a layer of glue.

Figure 11A:
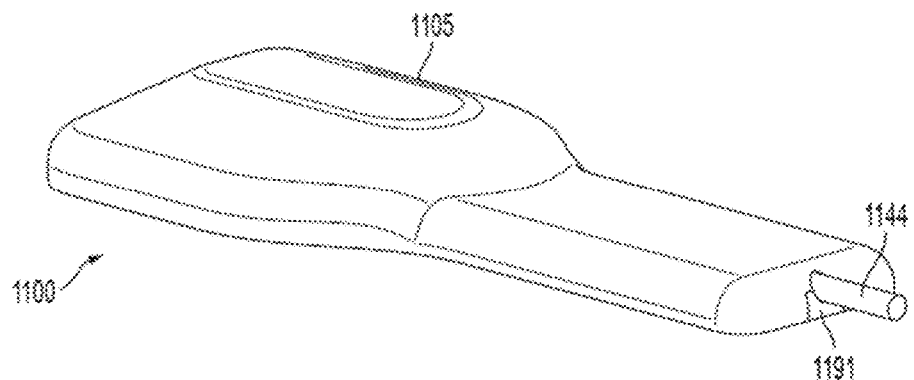
FIGS. 11A and 11B are diagrams showing an isometric view of a mouthpiece in accordance with an illustrative embodiment of the invention.
Figure 11B:
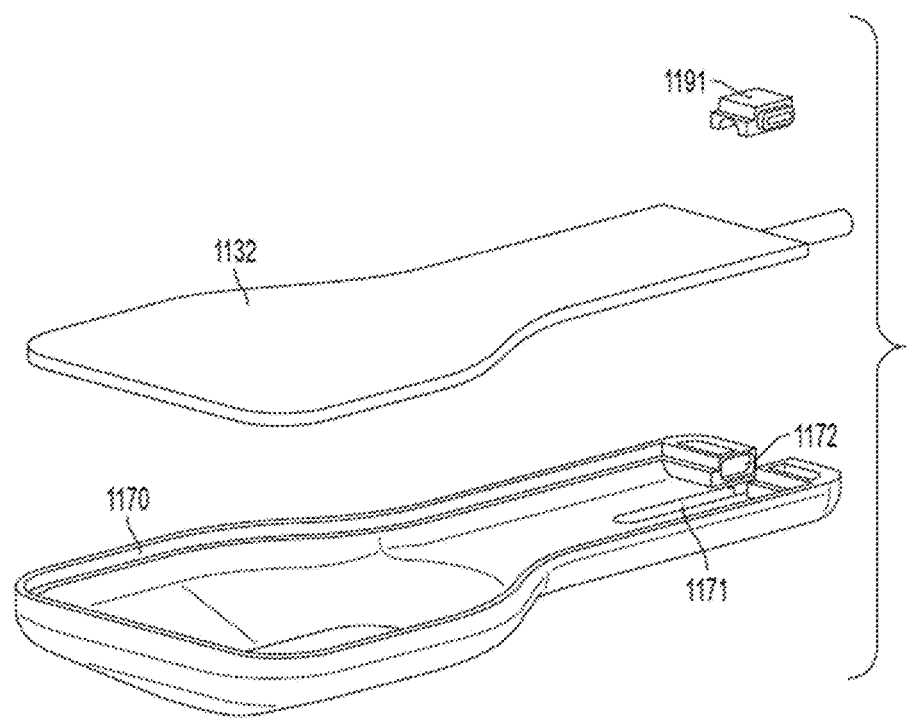
Figure 11C:
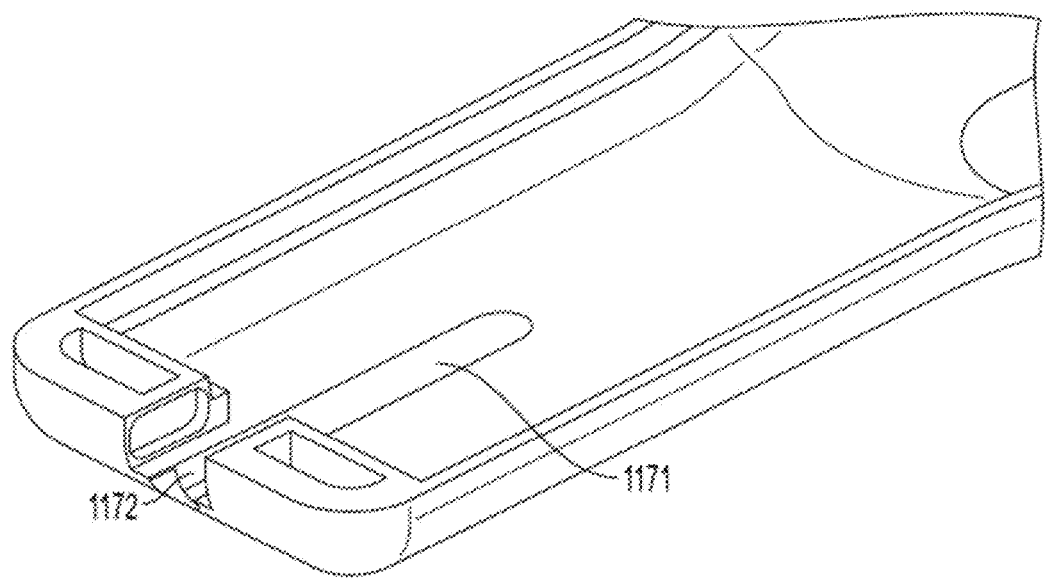
FIG. 11C is a diagram showing an isometric view of the mouthpiece in accordance with an illustrative embodiment of the invention.

FIGS. 11A-11C show a mouthpiece 1100. The mouthpiece 1100 includes an outer shell 1105, a printed circuit board 1132, a cable 1144, and a fastener 1191. The outer shell includes a glue well 1170, a valley 1171, and a port 1172 shaped to accommodate the fastener 1191. The glue well 1170 can accommodate an epoxy or other adhesive that connects the outer shell 1105 to the printed circuit board 1132. The cable 1144 is attached to the printed circuit board 1132 via solder, ribbon cable, or other mechanical connector. The cable rests in the valley 1171 before exiting at port 1172. An O-ring surrounds the cable 1144 at the port 1172. The fastener 1191 attaches to the outer shell 1105 at the position of the port 1172. The fastener applies a force to the O-ring that holds the cable in place at the port. The O-ring together with the fastener 1172 protect the cable from pulling or tugging by the patient. In some embodiments, the O-ring and the fastener 1172 provide resistance to both bending and tensile strain. In some embodiments, an epoxy or adhesive surrounds the cable 1144 at the port 1172.

Figure 12:
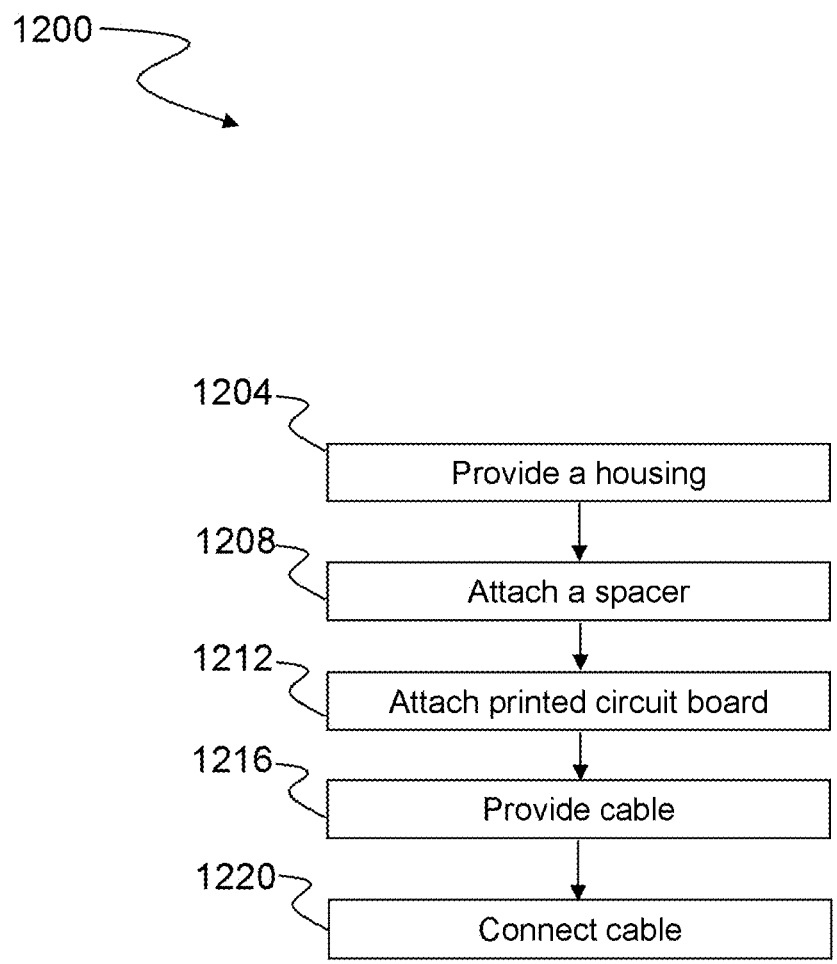
FIG. 12 is a flow chart illustrating a method in accordance with one embodiment for manufacturing a mouthpiece.

FIG. 12 shows a method 1200 of manufacturing a mouthpiece such as the mouthpiece shown in FIG. 5. Initially, a housing is provided (step 1204). A spacer is attached to the housing (step 1208). In some embodiments, the spacer is molded directly onto the housing. In some embodiments, the spacer attached to the housing via an adhesive or glue. The housing is attached to the printed circuit board (step 1212). In some embodiments, the housing is molded directly onto the printed circuit board. The molded housing can wrap around the edge of the printed circuit board and create a lip on the bottom side of the printed circuit board for better engagement. In some embodiments, features can be added to the printed circuit board (e.g., countersunk holes, beveled edge of the board, stepped edge of the board, tongue and groove edge of the board) such that when the molded housing is molded onto the board, the plastic hardens around the features to create better engagement. In some embodiments, the housing is attached to the printed circuit board via an adhesive and/or mechanical clips. In some embodiments, the housing is attached to the printed circuit board by a mechanical bond. In some embodiments, the housing is attached to the printed circuit board by a chemical bond. In some embodiments, the attached housing covers and encapsulates surface mounted electronics on the printed circuit board, while leaving the electrode array exposed such that the electrode array can be placed in contact with a patient's tongue for NINM therapy. A cable is provided (step 1216). The cable is connected to the printed circuit board (step 1220). In some embodiments, the cable is connected to the printed circuit board prior to the housing being molded onto the printed circuit board. The cable can be partially encapsulated by the housing after the molding process. In some embodiments, the housing is molded onto the printed circuit board in two steps. In a first step a first shot of plastic can be molded onto the board, where the mold temperatures and pressures are low enough that it is not hazardous to the electrical components on the board. The first shot can be used to pot the components, thereby protecting them. The first shot can be a softer material (TPE, TPU) or a rigid material with a lower mold pressure and/or temperature (Polyamide, Polyolefin). A second shot is molded over at least a portion of the first shot, where mold temperatures and pressures are higher than the first shot. This second shot may be of harder, more durable materials (e.g., nylon or glass filled nylon, ABS, PC, etc.). In some embodiments, the housing is molded onto, and completely surrounds the printed circuit board, such that only the electrode array is not covered by the housing. In this situation, the printed circuit board material would not come into contact with the patient, thereby protecting the patient in the case of harmful printed circuit board materials. In some embodiments, the electrode array is non-planar with the printed circuit board (e.g., the electrode array can protrude by a distance in the range of 0.1 to 1 mm from the printed circuit board). In some embodiments, the electrode array is an array of pins that protrude from the printed circuit board. The array of pins remains exposed after molding the housing onto the printed circuit board.

Figure 13A:
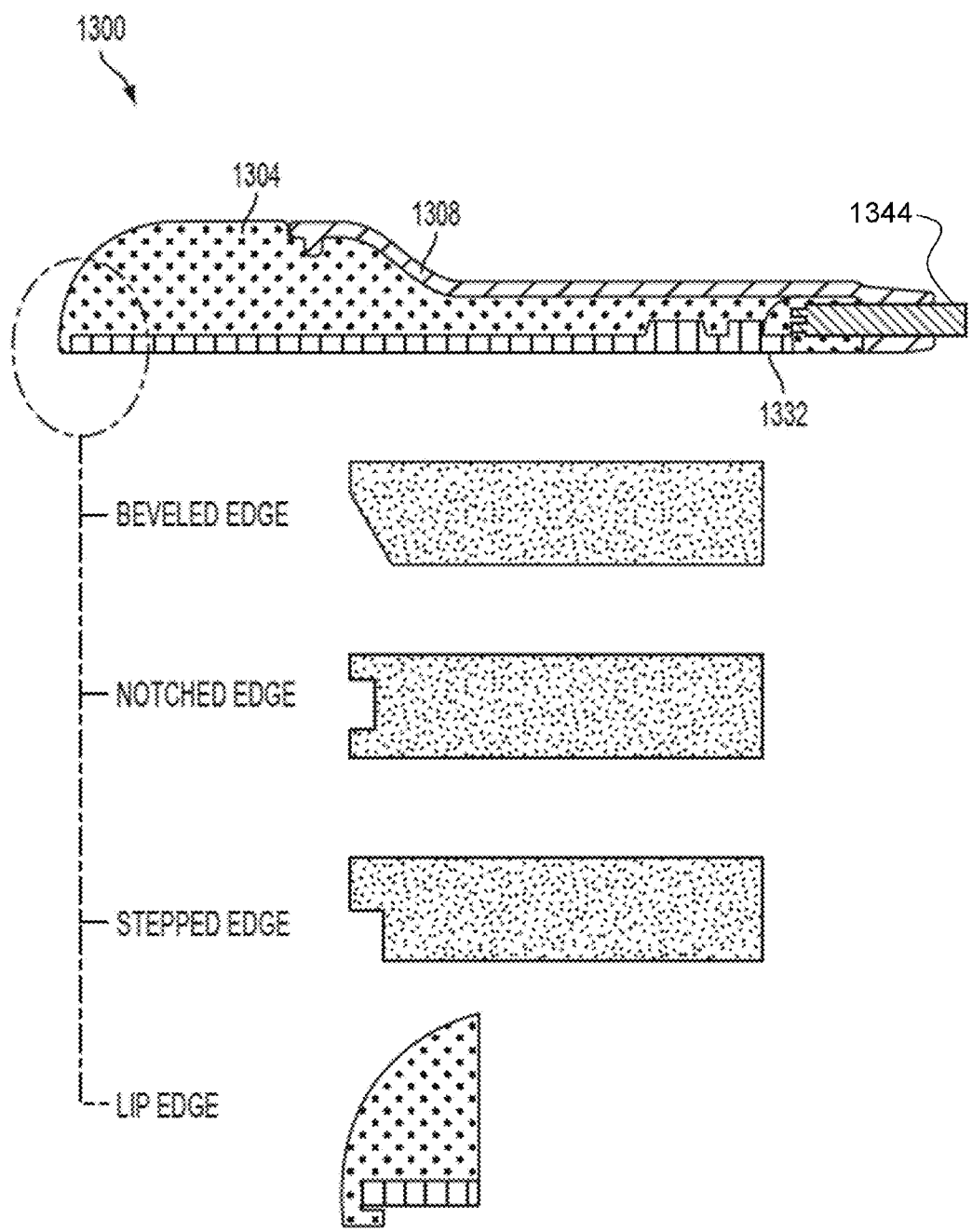
FIGS. 13A-B are diagrams showing an overmolded mouthpiece in accordance with an illustrative embodiment of the invention.
Figure 13B:
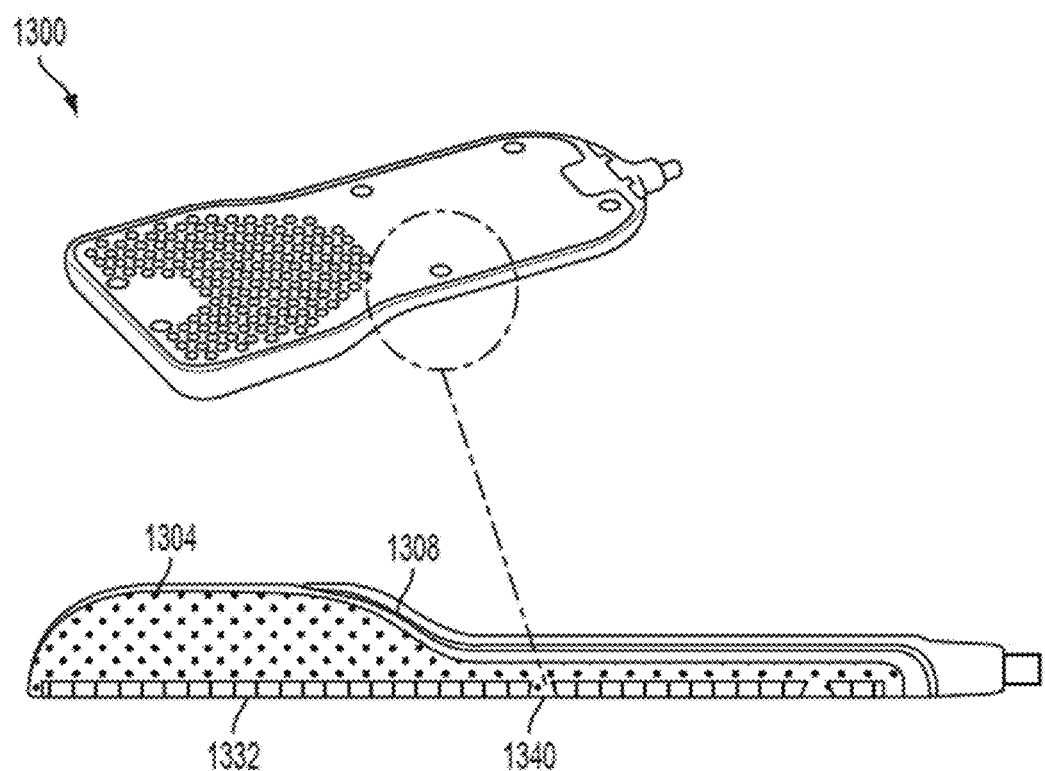

FIGS. 13A and 13B show a mouthpiece 1300 that has been manufactured by overmolding a housing 1304 directly onto a printed circuit board 1332. The mouthpiece 1300 includes a spacer 1308 and a cable 1344. In some embodiments, the printed circuit 1332 board includes features for mechanically engaging the molded housing 1304 (e.g., a beveled edge of the board, a stepped edge of the board, a notched edge of the board etc.). In some embodiments, the molded housing 1304 can wrap around the edge of the printed circuit board 1332 and create a lip on the bottom side of the printed circuit board to mechanically engage the printed circuit board 1332. In some embodiments, the printed circuit board includes countersunk holes 1340. The countersunk holes are filled with plastic as the housing 1304 is molded onto the printed circuit board. A rivet forms inside the countersunk hole 1340, with the rivet being an integral portion of the housing 1304. The tapered shape of the rivet provides a force that holds the printed circuit board 1332 in mechanical contact with the housing 1304.

Figure 14:
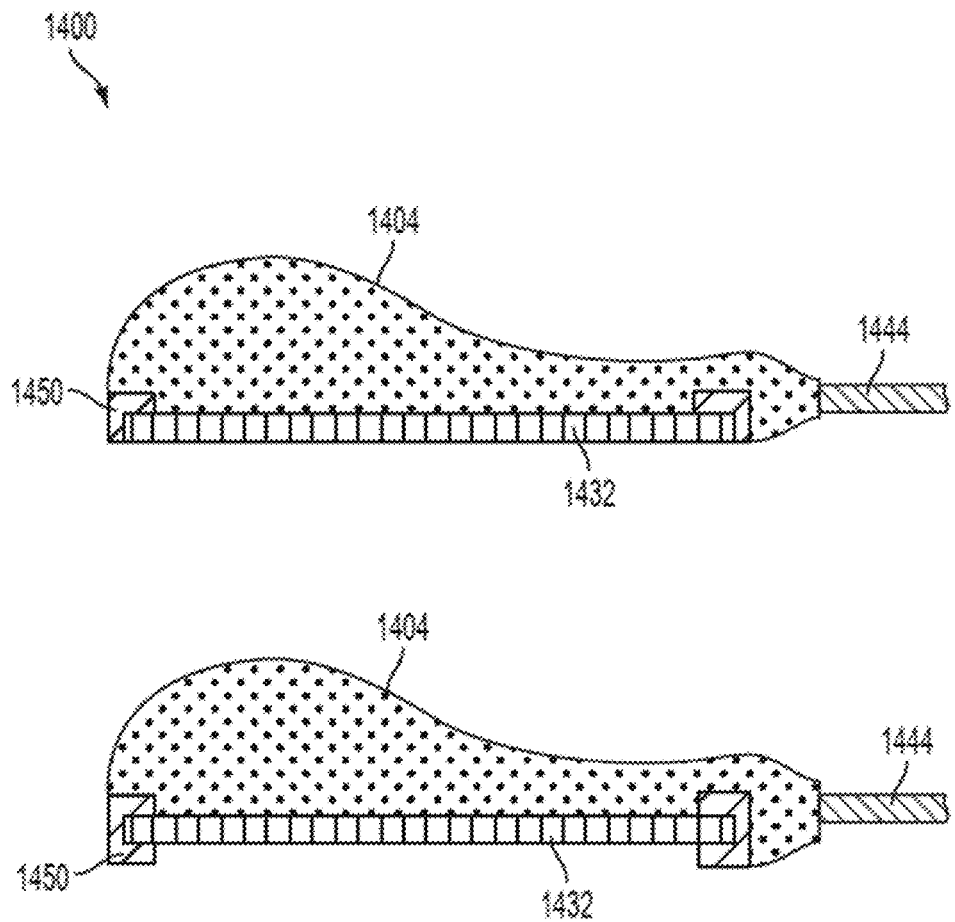
FIG. 14 is a diagram showing an overmolded mouthpiece in accordance with an illustrative embodiment of the invention.

FIG. 14 shows a mouthpiece 1400 according to a two shot injection molding manufacturing method wherein a shot refers to the volume of material that is used to fill a mold cavity and compensate for material shrinkage. The mouthpiece 1400 includes a housing 1404, a printed circuit board 1432, a cable 1444, and a frame 1450. The frame 1450 is formed around the printed circuit board (one or both sides) 1432 during a first shot, which provides a seal between the printed circuit board and the external environment. The housing 1404 is formed around the printed circuit board 1432 and frame 1450 during a second shot, thereby encapsulating the components on the printed circuit board 1432 and chemically bonding to the frame 1450. The first and second shots can be rigid, elastomeric, or a combination of both.

The terminology used herein is for the purpose of describing particular embodiments and is not intended to be limiting of the inventive concepts. It will be understood that, although the terms first, second, third etc. are used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present application.

While the present inventive concepts have been particularly shown and described above with reference to exemplary embodiments thereof, it will be understood by those of ordinary skill in the art, that various changes in form and detail can be made without departing from the spirit and scope of the present inventive concepts described and defined by the following claims.

What is claimed is:

1. A mouthpiece for providing non-invasive neuromodulation to a patient, the mouthpiece comprising:
   an elongated housing having an anterior region and a posterior region, the elongated housing having (i) a non-planar exterior top surface and (ii) an interpenetrating network of ribs disposed within the housing, at least some of the ribs aligned parallel to a longitudinal axis of the elongate housing and at least some of the ribs aligned perpendicular to a longitudinal axis of the elongated housing the interpenetrating network of ribs forming pockets in a posterior region of the elongated housing and elastically responding to biting forces generated by the patient;

a spacer attached to the top surface of the housing for limiting contact between a patient's upper teeth and the exterior top surface of the elongated housing; and a printed circuit board mounted to a bottom portion of the elongated housing, the printed circuit board having a plurality of electrodes for delivering subcutaneous local electrical stimulation to the patient's tongue.

2. The mouthpiece of claim 1 further comprising ribs aligned parallel to a longitudinal axis of the elongated housing.

3. The mouthpiece of claim 1 further comprising ribs aligned perpendicular to a longitudinal axis of the elongated housing.

4. The mouthpiece of claim 1 further comprising ribs aligned parallel to a longitudinal axis of the elongated housing and ribs aligned perpendicular to a longitudinal axis of the elongated housing.

5. The mouthpiece of claim 1 further comprising integrated circuits located in the pockets.

6. The mouthpiece of claim 2 wherein the ribs have a rectangular cross section.

7. The mouthpiece of claim 2 wherein the ribs are comprised of arches.

8. The mouthpiece of claim 1 further comprising one or more columns extending away from an interior surface of the elongated housing, the one or more columns configured to contact the mounted printed circuit board.

9. The mouthpiece of claim 1 wherein the structural elements can withstand a force of 700 Newtons without causing plastic deformation of the mouthpiece.

10. The mouthpiece of claim 1 further comprising a rectangular sheet embedded on an interior surface of the elongated housing and located in a posterior region of the elongated housing, the rectangular sheet connecting the interpenetrating network of ribs.

11. The mouthpiece of claim 2 further comprising a curvilinear sheet embedded on an interior surface of the elongated housing and located in a region connecting the anterior region and the posterior region of the elongated housing, the curvilinear sheet connecting the ribs aligned parallel to a longitudinal axis of the elongated housing.

12. A mouthpiece for providing non-invasive neuromodulation to a patient, the mouthpiece comprising:

an elongated housing having an anterior region and a posterior region, the elongated housing having (i) a non-planar exterior top surface and (ii) an interpenetrating network of ribs disposed within the housing, at least some of the ribs aligned parallel to a longitudinal axis of the elongate housing and at least some of the ribs aligned perpendicular to a longitudinal axis of the elongated housing, the interpenetrating network of ribs forming pockets in a posterior region of the elongated housing and elastically responding to biting forces generated by the patient; and a printed circuit board mounted to a bottom portion of the elongated housing, the printed circuit board having a plurality of electrodes for delivering subcutaneous local electrical stimulation to the patient's tongue.

13. The mouthpiece of claim 12 further comprising ribs aligned parallel to a longitudinal axis of the elongated housing.

14. The mouthpiece of claim 12 further comprising ribs aligned perpendicular to a longitudinal axis of the elongated housing.

15. The mouthpiece of claim 12 further comprising ribs aligned parallel to a longitudinal axis of the elongated housing and ribs aligned perpendicular to a longitudinal axis of the elongated housing.

16. The mouthpiece of claim 12 further comprising integrated circuits located in the pockets.

17. The mouthpiece of claim 13 wherein the ribs have a rectangular cross section.

18. The mouthpiece of claim 13 wherein the ribs are comprised of arches.

19. The mouthpiece of claim 12 further comprising one or more columns extending away from an interior surface of the elongated housing, the one or more columns configured to contact the mounted printed circuit board.

20. The mouthpiece of claim 12 wherein the structural elements can withstand a force of 700 Newtons without causing plastic deformation of the mouthpiece.

* * * * *